(12) United States Patent
Shirasaki et al.

(10) Patent No.: US 7,491,705 B2
(45) Date of Patent: Feb. 17, 2009

(54) ALPHA-KETOAMIDE DERIVATIVE, AND PRODUCTION METHOD AND USE THEREOF

(75) Inventors: Yoshihisa Shirasaki, Kobe (JP); Hiroyuki Miyashita, Kumamoto (JP); Masayuki Nakamura, Kobe (JP); Jun Inoue, Kobe (JP)

(73) Assignee: Senju Pharmaceutical Co., Ltd., Osaka (JP)

( * ) Notice: Subject to any disclaimer, the term of this patent is extended or adjusted under 35 U.S.C. 154(b) by 161 days.

(21) Appl. No.: 10/582,015

(22) PCT Filed: Dec. 8, 2004

(86) PCT No.: PCT/JP2004/018692

§ 371 (c)(1),
(2), (4) Date: Jul. 25, 2006

(87) PCT Pub. No.: WO2005/056519

PCT Pub. Date: Jun. 23, 2005

(65) Prior Publication Data

US 2007/0004643 A1 Jan. 4, 2007

(30) Foreign Application Priority Data

Dec. 12, 2003 (JP) ............................. 2003-415764
Aug. 11, 2004 (JP) ............................. 2004-234164

(51) Int. Cl.
*A61K 38/05* (2006.01)
(52) U.S. Cl. ..................................................... 514/19
(58) Field of Classification Search ...................... None
See application file for complete search history.

(56) References Cited

U.S. PATENT DOCUMENTS

| 5,444,042 | A | 8/1995 | Bartus et al. |
| 5,514,694 | A | 5/1996 | Powers et al. |
| 5,541,290 | A | 7/1996 | Harbeson et al. |
| 5,610,297 | A | 3/1997 | Powers |
| 5,650,508 | A | 7/1997 | Powers |
| 5,763,576 | A | 6/1998 | Powers |
| 6,150,378 | A | 11/2000 | Chatterjee et al. |
| 6,235,929 | B1 | 5/2001 | Powers |
| 6,686,335 | B1 | 2/2004 | Mallamo et al. |

FOREIGN PATENT DOCUMENTS

| WO | 92/12140 | 7/1992 |
| WO | 94/00095 | 1/1994 |
| WO | 98/50065 | 11/1998 |
| WO | 02/078670 | 10/2002 |

OTHER PUBLICATIONS

Harbeson et al., "Stereospecific Synthesis of Peptidyl .alpha.-Keto Amides as Inhibitors of Calpain" J. Med. Chem., 1994, 37, 2918-29.*

Carragher "Calpain Inhibition: A Therapeutic Strategy Targeting Multiple Disease States," Curr. Pharm. Des., 2006, 12, 615-38.*

S. L. Harbeson et al., "Stereospecific Synthesis of Peptidyl α-Keto Amides as Inhibitors of Calpain", J. Med. Chem., vol. 37, No. 18, pp. 2918-2929, 1994.

E. Caba et al., "Peptideyl α-Keto Amide Inhibitor of Calpain Blocks Excitotoxic Damage without Affecting Signal Transduction Events", Journal of Neuroscience Research, vol. 67, No. 6, pp. 787-794, 2002.

K. A. Josef et al., "Potent Peptide α-Ketohydroxamate Inhibitors of Recombinant Human Calpain I", Bioorganic & Medicinal Chemistry Letters, vol. 11, No. 19, pp. 2615-2617, 2001.

I. O. Donkor et al., "Significance of Hydrogen Bonding at the $S_1'$ Subsite of Calpain I", Bioorganic & Medicinal Chemistry Letters, vol. 11, No. 13, pp. 1753-1755, 2001.

R. L. DeBiasi et al., "Calpain Inhibition Protects against Virus-Induced Apoptotic Myocardial Injury", Journal of Virology, vol. 75, No. 1, pp. 351-361, Jan. 2001.

I. O. Donkor et al., "Synthesis and Calpain Inhibitory Activity of α-Ketoamides with 2,3-Methanoleucine Stereoisomers at the $P_2$ Position", Bioorganic & Medicinal Chemistry Letters, vol. 10, No. 22, pp. 2497-2500, 2000.

J. F. Harriman et al., "Efficacy of Novel Calpain Inhibitors in Preventing Renal Cell Death", The Journal of Pharmacology and Experimental Therapeutics, vol. 294, No. 3, pp. 1083-1087, 2000.

(Continued)

*Primary Examiner*—Cecilia Tsang
*Assistant Examiner*—Christina Marchetti Bradley
(74) *Attorney, Agent, or Firm*—Wenderoth, Lind & Ponack, L.L.P.

(57) ABSTRACT

The present invention provides a compound represented by the formula (I):

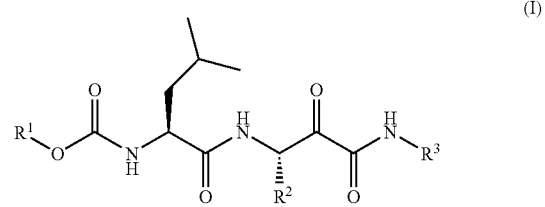

(wherein $R^1$ is a lower alkyl substituted by a lower alkoxy or a heterocyclic group, or a heterocyclic group;

$R^2$ is a lower alkyl optionally substituted by a phenyl; and $R^3$ is a lower alkyl optionally substituted by a halogen, a lower alkoxy or a phenyl, or a fused polycyclic hydrocarbon group), which is well absorbed orally, exhibits durability of good blood level and has potent calpain inhibitory activity.

6 Claims, 1 Drawing Sheet

OTHER PUBLICATIONS

K. E. Saatman et al., "Behavioral Efficacy of Posttraumatic Calpain Inhibition is not Accompanied by Reduced Spectrin Proteolysis, Cortical Lesion, or Apoptosis", Journal of Cerebral Blood Flow and Metabolism, vol. 20, No. 1, pp. 66-73, 2000.

T. James et al., "New Inhibitors of Calpain Prevent Degradation of Cytoskeletal and Myelin Proteins in Spinal Cord In Vitro", Journal of Neuroscience Research, vol. 51, No. 2, pp. 218-222, 1998.

Z. Li et al., "Novel Peptidyl α-Keto Amide Inhibitors of Calpains and Other Cysteine Proteases", Journal of Medicinal Chemistry, vol. 39, No. 20, pp. 4089-4098, 1996.

K. E. Saatman et al., "Calpain Inhibitor AK295 Attenuates Motor and Cognitive Deficits Following Experimental Brain Injury in the Rat", Proceedings of the National Academy of Sciences of the United States of America, vol. 93, No. 8, pp. 3428-3433, Apr. 1996.

R. T. Bartus et al., "Calpain Inhibitor AK295 Protects Neurons from Focal Brain Ischemia", Stroke, vol. 25, No. 11, pp. 2265-2270, Nov. 1994.

C. Wu et al., "High-Performance Liquid Chromatographic Reversed-Phase and Normal-Phase Separation of Diastereomeric α-ketoamide Calpain Inhibitors", Journal of Chromatography A, vol. 684, No. 2, pp. 243-249, 1994.

I. O. Donkor et al., "Design, Synthesis, Molecular Modeling Studies, and Calpain Inhibitory Activity of Novel α-Ketoamides Incorporating Polar Residues at the $P_1'$-Position", Journal of Medicinal Chemistry, vol. 47, No. 1, pp. 72-79, 2004.

P. Mathur et al., "Cellular Events Preceding Acetaminophen Cataractogenesis Studied by Confocal Fluorescence Microscopy", Journal of Ocular Pharmacology and Therapeutics, vol. 19, No. 5, pp. 483-492, 2003.

W. Lubisch et al., "Benzoylalanine-Derived Ketoamides Carrying Vinylbenzyl Amino Residues: Discovery of Potent Water-Soluble Calpain Inhibitors with Oral Bioavailability", J. Med. Chem., vol. 46, No. 12, pp. 2404-2412, 2003.

* cited by examiner

ALPHA-KETOAMIDE DERIVATIVE, AND PRODUCTION METHOD AND USE THEREOF

This application is a U.S. national stage of International Application No. PCT/JP2004/018692 filed Dec. 8, 2004.

TECHNICAL FIELD

The present invention relates to a novel α-ketoamide derivative having calpain inhibitory activity. Also, the present invention relates to a medicament comprising the novel α-ketoamide derivative.

BACKGROUND ART

Calpain is one of the intracellular proteases ubiquitously present in a living body, which is activated by $Ca^{2+}$. It has been elucidated to this day that abnormal activation of calpain is involved in various diseases such as cerebral apoplexy, subarachnoid hemorrhage, Alzheimer's disease, ischemic disease, muscular dystrophy, cataract, platelet aggregation disorder, arthritis and the like (see Non-patent literature 1).

On the other hand, it has been reported that a calpain inhibitor is effective for maintaining permeability of lens in an experimental cataract model of cultured lens and is useful as a therapeutic agent for cataract, etc. (see Non-patent literature 2, Patent literature 1).

Examples of calpain inhibitors which have been so far reported are peptide halomethane derivatives, peptide diazomethane derivatives, peptidyl aldehyde derivatives, peptidyl α-ketoamide derivatives and the like (for example, see Patent literatures 2 to 6, Non-patent literatures 3 to 4).

(Patent literature 1) WO 93/23032

(Patent literature 2) JP-B-29229/1994

(Patent literature 3) EP-A-0771565

(Patent literature 4) U.S. Pat. No. 6,057,290

(Patent literature 5) JP-A-147564/1998

(Patent literature 6) WO 92/12140

(Non-patent literature 1) Trends in Pharmacological Sciences, vol. 15, page 412, 1994

(Non-patent literature 2) Current Eye Research, vol. 10, Pages 657 to 666, 1991

(Non-patent literature 3) The Biochemical Journal, vol. 253, pages 751 to 758, 1988

(Non-patent literature 4) Journal of Medicinal Chemistry, vol. 35, pages 216 to 220, 1992

DISCLOSURE OF THE INVENTION

An object of the present invention is to provide a compound having potent calpain inhibitory activity, which is well absorbed orally and exhibits durability of good blood level.

The present inventors have conducted intensive studies to create a calpain inhibitor having tissue transport and absorbability, especially good oral absorbability and durability of good blood level. The present inventors designed α-ketoamide derivatives having an amphipathic group in the molecule thereof, and found among those compounds a compound having calpain protease inhibitory activity and good oral absorbability. They have conducted further studies and thus completed the present invention.

Namely, the present invention relates to
(1) A compound represented by the formula (I)

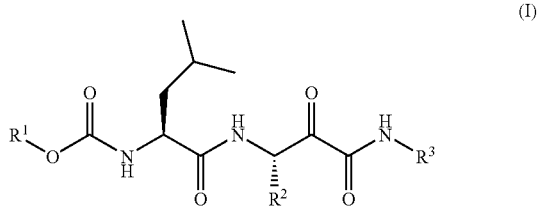

wherein
$R^1$ is a lower alkyl substituted by a lower alkoxy or a heterocyclic group, or a heterocyclic group;
$R^2$ is a lower alkyl optionally substituted by a phenyl; and
$R^3$ is hydrogen, a lower alkyl optionally substituted by a halogen, a lower alkoxy or a phenyl, or a fused polycyclic hydrocarbon group, (2) the compound according to the above (1), wherein the lower alkyl represented by $R^1$ which is substituted by a lower alkoxy is a group the formula (IIa)

in which $R^4$ is a lower alkyl, $R^5$ is a lower alkylene, and m is an integer of 1 to 6, (3) the compound according to the above (1), wherein the lower alkyl represented by $R^1$ which is substituted by a lower alkoxy is a group of the formula (IIb)

in which n is an integer of 1 to 6, (4) the compound according to the above (1), wherein the heterocyclic group which is a substituent for the lower alkyl represented by $R^1$ is pyridyl optionally having a lower alkyl, (5) the compound according to the above (1), wherein the hetero atom of the heterocyclic group represented by $R^1$ is an oxygen atom, (6) the compound according to any one of the above (1) to (5), wherein the lower alkyl represented by $R^3$ is cyclopropyl, (7) ((1S)-1-((((1S)-1-benzyl-2,3-dioxo-3-(cyclopropylamino)propyl)amino)carbonyl)-3-methylbutyl)carbamic acid 2-methoxyethyl ester, ((1S)-1-((((1S)-1-benzyl-2,3-dioxo-3-(cyclopropylamino)propyl)amino)carbonyl)-3-methylbutyl)carbamic acid 5-methoxy-3-oxapentyl ester, ((1S)-1-((((1S)-1-benzyl-2,3-dioxo-3-(cyclopropylamino)propyl)amino)carbonyl)-3-methylbutyl)carbamic acid 8-methoxy-3,6-dioxaoctyl ester, ((1S)-1-((((1S)-1-benzyl-2,3-dioxo-3-(cyclopropylamino)propyl)amino)carbonyl)-3-methylbutyl)carbamic acid 11-methoxy-3,6,9-trioxaundecanyl ester, or ((1S)-1-((((1S)-1-benzyl-3-(cyclopropylamino)-2,3-dioxopropyl)amino)carbonyl)-3-methylbutyl)carbamic acid 2-(pyridin-2-yl)ethyl ester, (8) a medicament comprising the compound according to the above (1) or (7), (9) the medicament according to the above (8), which is a calpain inhibitor,

(10) the medicament according to the above (9), which is a therapeutic agent for a disease related to calpain, and

(11) the medicament according to the above (10), wherein the disease related to calpain is ischemic disease, immunologic disease, multiple sclerosis, Alzheimer's disease, osteoporosis, diseases caused by brain tissue damage, cataract, glaucoma, retinal disease, retinochoroiditis, posterior eyeball complications due to photocoagulation or a disease involving neovascularization.

The compound of the present invention is a calpain inhibitor which is well absorbed orally and exhibits durability of good blood level, and thus said compound can be used as an agent for prophylaxis or treatment of diseases related to calpain such as ischemic disease, immunologic disease, multiple sclerosis, Alzheimer's disease, osteoporosis, diseases caused by brain tissue damage, cataract, glaucoma, retinochoroiditis disease (diabetic retinopathy, retinal vein occulusion, macular degeneration, retinitis pigmentosa, hypertensive retinopathy, retinal detachment, etc.), posterior eyeball complications due to photocoagulation (e.g. macular edema, retinal detachment, optic neuritis, visual field defect, light sense defect, dyschromatopsia, etc.), a disease involving neovascularization and the like.

Since the compound of the present invention has high oral absorbability, a medicament containing the compound of the present invention can be administered orally.

In addition, the compound of the present invention has low toxicity, and thus can be used safely.

BEST MODE FOR CARRYING OUT THE INVENTION

Figure 1:
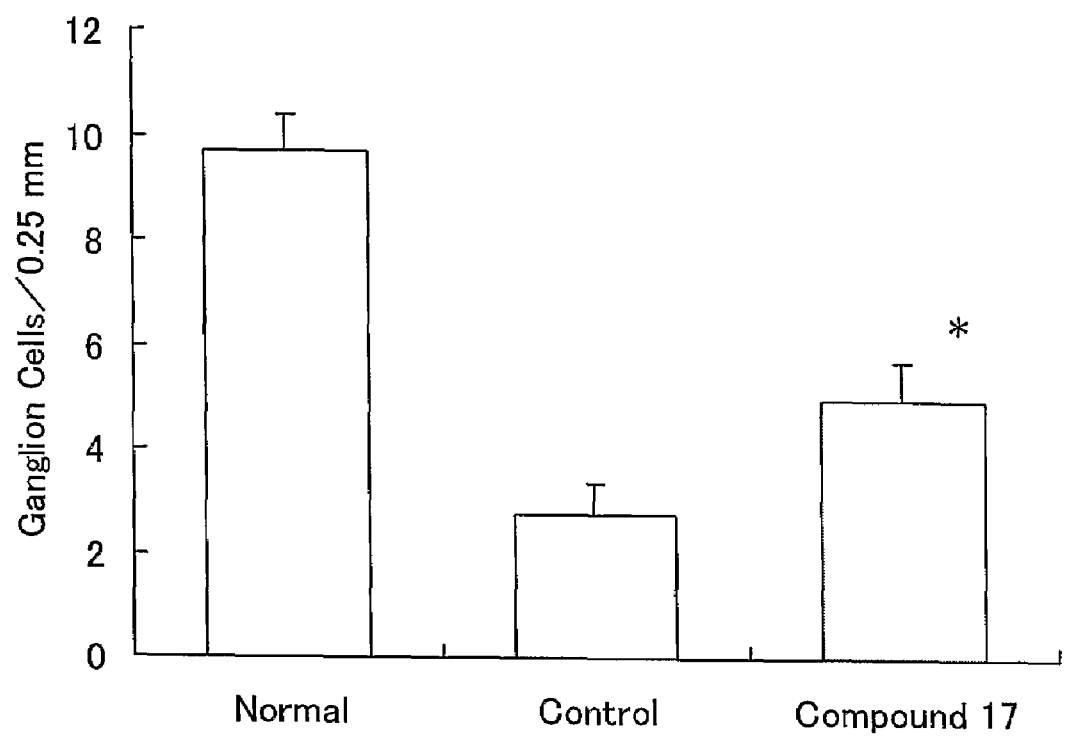
FIG. 1: A graph showing viable cell count in the ganglion cell layer after 7-day retinal ischemia reperfusion in rats. Each column represents the mean±S.E. In the graph, "Normal" means a normal group (n=8), "Control" means a control group (n=8), and "Compound 17" means a group to which compound 17 is administered (n=9). The symbol (*) shows significant difference (P<0.05, Student's t-test (both sides)) from the control group.

In the above formula (I), preferable examples of lower alkyl as the lower alkyl substituted by a lower alkoxy or a heterocyclic group represented by $R^1$ include a straight or branched $C_{1-6}$ alkyl group, specifically, methyl, ethyl, propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1-ethyl-2-methylpropyl, 1,1,2-trimethylpropyl, etc. More preferable examples of the lower alkyl for $R^1$ include a straight or branched $C_{2-3}$ alkyl group, and the most preferable example includes ethyl.

A preferable example of the lower alkoxy which is a substituent for the lower alkyl represented by $R^1$ includes a $C_{1-6}$ lower alkoxy such as methoxy, ethoxy, propoxy, isopropoxy, butoxy, isobutoxy, sec-butoxy, tert-butoxy, pentyloxy, isopentyloxy, neopentyloxy, tert-pentyloxy, 1-methylbutoxy, 2-methylbutoxy, 1,2-dimethylpropoxy, hexyloxy, 1-methylpentyloxy, 2-methylpentyloxy, 3-methylpentyloxy, 4-methylpentyloxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1-ethyl-2-methylpropoxy, 1,1,2-trimethylpropoxy, etc. Said alkoxy group which is further substituted by said lower alkoxy may be used preferably.

A preferable example of the lower alkyl represented by $R^1$ which is substituted by a lower alkoxy includes a group the formula (IIa)

(IIa)

in which $R^4$ is a lower alkyl, $R^5$ is a lower alkylene, and m is an integer of 1 to 6, and more preferable example includes a group of the formula (IIb)

(IIb)

in which n is an integer of 1 to 6.

Examples of the lower alkyl represented by $R^4$ in the above formula (IIa) include methyl, ethyl, propyl, isopropyl, butyl, isobutyl, sec-butyl, tert-butyl, etc., preferably methyl, isopropyl or tert-butyl, and more preferably methyl.

A preferable example of the lower alkylene represented by $R^5$ in the above formula (IIa) includes a $C_{1-4}$ alkylene, specifically methylene, ethylene, trimethylene and tetramethylene, and a more preferable example is ethylene. The lower alkylene represented by $R^5$ may have a substituent. Examples of the substituent include methyl, ethyl, etc.

In the above formula (IIa), m is an integer of 1 to 6, preferably an integer of 2 to 5. In the above formula (IIb), n is an integer of 1 to 6, preferably an integer of 1 to 5, and more preferably an integer of 2 to 5.

A preferable example of the heterocyclic group which is a substituent for the lower alkyl represented by $R^1$ includes a pyridyl optionally having a lower alkyl. Examples of the pyridyl include 2-pyridyl, 3-pyridyl and 4-pyridyl. A preferable example of the lower alkyl optionally included in said pyridyl is a $C_{1-3}$ lower alkyl, specifically, methyl, ethyl, propyl, isopropyl, etc.

Examples of the heterocyclic group represented by $R^1$ include 5- to 7-membered aromatic group containing one to three atom(s) identically or differently selected from the group consisting of sulfur, oxygen and nitrogen, or partially or fully reduced, saturated heterocyclic group, and specific examples thereof include furyl, thienyl, pyrrolyl, azepinyl, pyrazolyl, imidazolyl, oxazolyl, isoxazolyl, thiazolyl, isothiazolyl, 1,2,3-oxadiazolyl, triazolyl, tetrazolyl, thiadiazolyl, pyranyl, pyridyl, pyridazinyl, pyrimidinyl, pyrazinyl, morpholinyl, thiomorpholinyl, pyrrolidinyl, pyrrolinyl, imidazolidinyl, pyrazolidinyl, piperidinyl, piperazinyl, oxazolidinyl, isoxazolidinyl, thiazolidinyl, pyrazolidinyl, tetrahydrofuranyl, tetrahydropyranyl, tetrahydrothiophenyl, etc., preferably saturated heterocyclic group, more preferably 5- to 7-membered saturated heterocyclic group containing oxygen atom(s), and most preferably tetrahydrofuranyl, tetrahydropyranyl, etc.

Examples of the lower alkyl represented by $R^2$ are the same as the said lower alkyl as the lower alkyl substituted by a lower alkoxy or a heterocyclic group represented by $R^1$, and include preferably methyl, ethyl and isobutyl. The lower alkyl represented by $R^2$ is preferably substituted by a phenyl group. Preferable examples of such phenyl-substituted lower alkyl group include benzyl, phenethyl, etc.

Examples of the lower alkyl represented by $R^3$ are the same as the said lower alkyl as the lower alkyl substituted by a lower alkoxy or a heterocyclic group represented by $R^1$, and may include a cycloalkyl group. Such cycloalkyl group can be cyclopropane, cyclobutane, cyclopentane, cyclohexane, etc., among which cyclopropane and cyclobutane are preferable.

Examples of the halogen by which the above lower alkyl group may be substituted include fluorine, chlorine, bromine, etc., among which fluorine is preferable.

Examples of the fused polycyclic hydrocarbon group include indanyl, indenyl, naphthyl, pentalenyl, azulenyl, etc., among which indanyl is preferable.

In addition, the compounds of the present invention include a variety of solvates, polymorphs and pro-drugs.

The compounds of the present invention can be prepared, for example, according to the following method.

bonyl, etc.), optionally substituted phenyloxycarbonyl and optionally substituted $C_{7-10}$ aralkyloxycarbonyl (e.g. phenyl-$C_{1-4}$ alkyloxycarbonyl such as benzyloxycarbonyl, etc.). As the substituent, halogen (e.g. fluorine, chlorine, bromine, iodine, etc.), nitro or the like is used, and the number of such substituents is approximately 1 to 3. Preferable substituent may be tert-butoxycarbonyl (Boc).

Examples of the reducing agent used in the above reaction include lithium aluminum hydride, sodium borohydride, sodium bis(2-methoxyethoxy)aluminum hydride or the like, among which sodium borohydride is preferable. The reaction temperature is $-40°$ C. to $30°$ C., preferably $-20°$ C. to $0°$ C.

The compound (V) may be prepared by adding an amino-protecting group to an amino alcohol of the formula (IV) in a similar manner (step a').

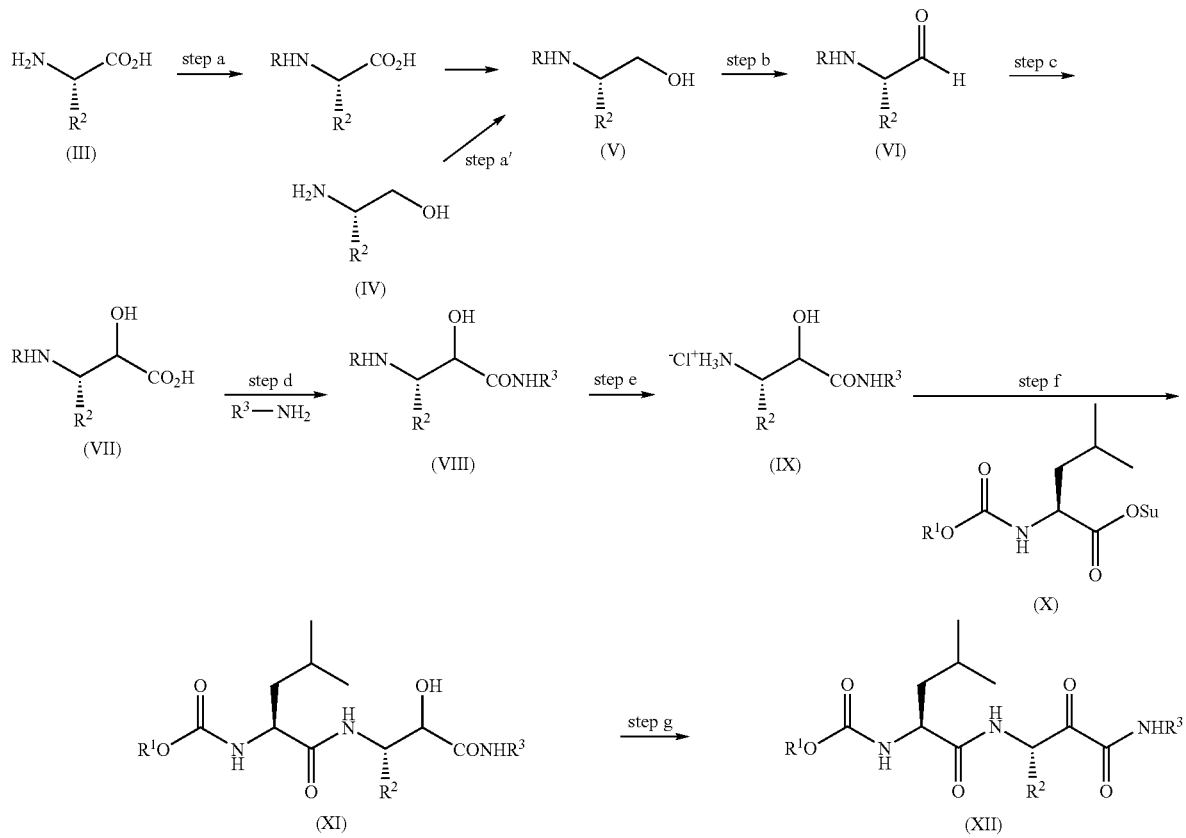

(wherein R is a protecting group, and other groups have the same meaning as defined above)

Step a is a process which comprises adding a protecting group into an amino group of amino acids of the formula (III), converting the protected product into a mixed anhydride, and reducing the mixed anhydride with a reducing agent to yield a compound of the formula (V) (hereinafter referred to as compound (V)). The above-mentioned addition and deprotection procedures of the protecting group(s) can be carried out by the conventional method. Examples of such protecting groups used are formyl, optionally substituted $C_{1-6}$ alkylcarbonyl (e.g. acetyl, propionyl, etc.), optionally substituted phenylcarbonyl, optionally substituted $C_{1-6}$ alkyl-oxycarbonyl (e.g. methoxycarbonyl, ethoxycarbonyl, tert-butoxycar- Step b is a process of oxidizing a compound (V) with dimethyl sulfoxide (DMSO) in the presence of an activating reagent for DMSO to yield a compound of the formula (VI) (hereinafter referred to as compound (VI)). The DMSO oxidation can be carried out by the conventional method. For example, the compound (V) is dissolved in DMSO alone or in a mixture of DMSO and a solvent not inhibiting the oxidation (e.g. tetrahydrofuran, dichloromethane, chloroform, ethyl acetate, benzene, ether, etc.), and diisopropylethylamine is usually added thereto in an amount of approximately 1- to 10-fold in a molar ratio per one mole of compound (V). The amount of DMSO used in the above reaction is approximately 1 to 20 mL to 1 g of compound (V). As the above activating reagent for DMSO, there are advantageously employed sulfur trioxide-pyridine complex, oxalyl chloride, dicyclohexylcarbodiimide, acetic anhydride or the like. Inter alia, sulfur trioxide-pyridine complex is preferably used.

Step c is a process of preparing a compound of the formula (VII) (hereinafter referred to as compound (VII)) as a diastereomer mixture, which comprises treating a compound (VI) with sodium hydrogen sulfite, reacting the product with sodium cyanide to yield a cyanohydrin compound, hydrolyzing the cyanohydrin compound with an acid or alkali catalyst without purification to yield a diastereomer mixture of α-hydroxy-β-amino acid, and adding again the above amino-protecting group to the α-hydroxy-β-amino acid in a similar manner.

This hydrolysis reaction is carried out by heating or by heating under reflux with an acid (e.g. hydrochloric acid, sulfuric acid, acetic acid, formic acid, etc.) or an alkali (e.g. sodium hydroxide, potassium hydroxide, barium hydroxide, etc.). The heating temperature is about 50° C. to about 100° C. As the solvent, a mixture of water and an organic solvent (e.g. dioxane, tetrahydrofuran, etc.) is preferably used.

hydrochloric acid to yield an amine hydrochloride of the formula (IX) (hereinafter referred to as compound (IX)). Such deprotection of amino-protecting group(s) can be carried out by the conventional method. For example, the compound (VIII) is dissolved in an organic solvent which is commonly used, and then the solution is stirred in the presence of an acid to remove the amino-protecting group(s). Examples of the acid include hydrochloric acid, trifluoroacetic acid, p-toluenesulfonic acid or the like. Alternatively, commercially available HCl/ethyl acetate or HCl/dioxane may be used to remove amino-protecting group(s). The reaction temperature is within the range of ice-cooling to room temperature.

Step f is a process of condensing a compound of the formula (IX) with a compound of the formula (X) (hereinafter referred to as compound (X)) in the presence of triethylamine to yield a compound of the formula (XI) (hereinafter referred to as compound (XI)).

The above compound (X) can be prepared according to the general reaction scheme given below.

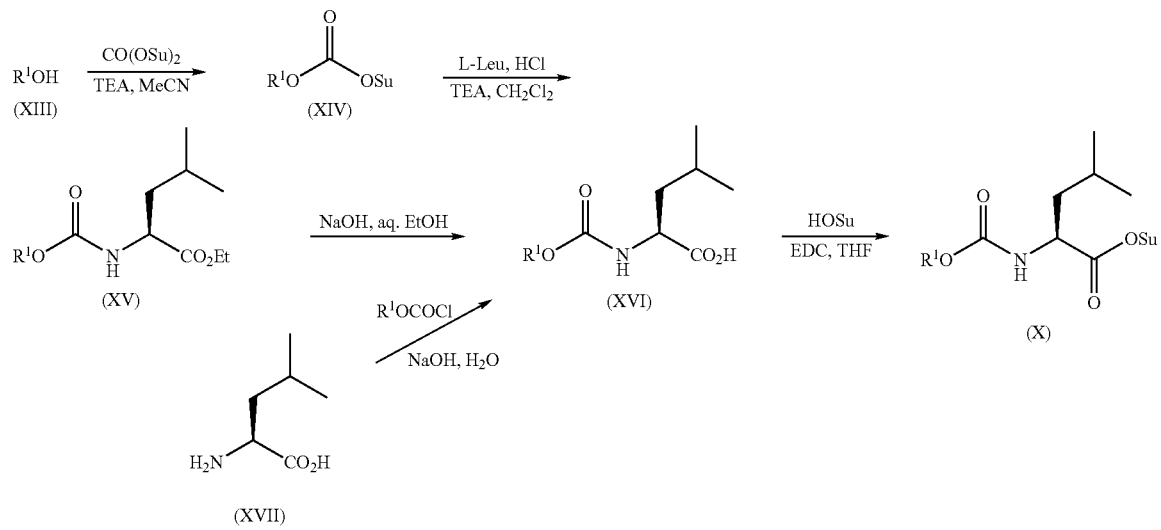

Step d is a process of condensing a compound (VII) with a variety of amines to yield a compound of the formula (VIII) (hereinafter referred to as VIII).

As to an amine, a suitable amine can be appropriately selected depending on the objective compound. Examples of such amines include ethylamine, propylamine, cyclopropylamine, butylamine, cyclobutylamine, methoxyethylamine, 2-phenoxyethylamine, 2-aminoindane, 2,2,2-trifluoroethylamine or the like.

It is preferable to carry out the above condensation in the presence of a dehydrative condensing agent such as 1-ethyl-3-(3-dimethylaminopropyl)carbodiimide hydrochloride, N,N-dicyclohexylcarbodiimide, etc. Examples of the organic solvent used in the condensation reaction include N,N-dimethylformamide, DMSO, tetrahydrofuran, dichloromethane, methanol, ethanol, benzene, toluene, ethyl acetate, etc., and a mixture thereof, among which N,N-dimethylformamide is preferable. The reaction temperature is within the range of ice-cooling to room temperature.

The step e is a process of deprotecting amino-protecting group(s) of a compound (VIII) under acidic condition with (wherein each symbol has the same meaning as defined above)

An alcohol of the formula (XIII) (hereinafter referred to as alcohol (XIII)) is reacted with di(N-succinimidyl) carbonate to yield a mixed carbonic ester of the formula (XIV), which is then condensed with L-leucine ethyl ester hydrochloride in the presence of triethylamine to yield a compound of the formula (XV). Alkali saponification of the compound (XV) affords a compound of the formula (XVI) (hereinafter referred to as (XVI)). Alternatively, the compound (XVI) may be obtained by direct reaction between L-leucine and chloroformate. The compound (XVI) is reacted with hydroxysuccinimide (HOSu) to yield a succinimide ester of the formula (X) (hereinafter referred to as compound (X)).

Step g is a process of oxidation of a compound (XI) to produce a compound of the formula (XII) (hereinafter referred to as compound (XII). The oxidation reaction is carried out by per se conventional methods, including those classified into (i) chromium oxidation such as pyridinium dichromate (PDC) oxidation, pyridinium chlorochromate (PCC) oxidation, Jones oxidation and Collins oxidation, and (ii) DMSO oxidation such as Swern oxidation, DMSO/sulfur trioxide-pyridine complex oxidation, DMSO/dicyclohexcyl-carbodiimide oxidation, DMSO/oxalyl chloride oxidation, Dess-Martin oxidation using Dess-Martin periodinane, hypohalogen acid oxidation and N-halogenocarboxylic amide oxidation, among which Dess-Martin oxidation is preferable. In carrying out Dess-Martin oxidation, the compound (XI) is dissolved in a commonly used organic solvent and Dess-Martin reagent is added thereto. Examples of the commonly used organic solvents include conventional solvents not adversely affecting the reaction or a mixture thereof, such as dichloromethane, N,N-dimethylformamide, DMSO, tetrahydrofuran, methanol, ethanol, benzene, toluene, ethyl acetate or the like, among which dichloromethane is preferable. The amount of the Dess-Martin reagent is approximately 1- to 20-fold mole equivalents, preferably 1- to 3-fold mole equivalents of the compound (XI). The reaction temperature is not particularly limited, and it is within the range of ice-cooling to room temperature. The compound (XII) thus obtained can be separated and purified by conventional methods including, for example, concentration, concentration in vacuo, solvent extraction, crystallization, recrystallization, solvent transfer, chromatography or the like.

The each step as mentioned above is carried out in a commonly used solvent not adversely affecting the reaction, and a mixture thereof. Examples of such a solvent not adversely affecting the reaction include dichloromethane, N,N-dimethylformamide, DMSO, tetrahydrofuran, methanol, ethanol, benzene, toluene, ethyl acetate or the like.

Specific examples of compounds (I) of the formula prepared according to the above method include
((1S)-1-((((1S)-1-benzyl-2,3-dioxo-3-(ethylamino)propyl)amino)carbonyl)-3-methylbutyl)carbamic acid 2-methoxyethyl ester (Compound 1),
((1S)-1-((((1S)-1-benzyl-2,3-dioxo-3-(ethylamino)propyl)amino)carbonyl)-3-methylbutyl)carbamic acid (3S)-tetrahydro-furan-3-yl ester (Compound 2),
((1S)-1-((((1S)-1-benzyl-2,3-dioxo-3-(ethylamino)propyl)amino)carbonyl)-3-methylbutyl)carbamic acid tetrahydro-4H-pyran-4-yl ester (Compound 3),
((1S)-1-((((1S)-1-benzyl-2,3-dioxo-3-(cyclopropylamino)propyl)amino)carbonyl)-3-methylbutyl)carbamic acid 2-methoxyethyl ester (Compound 4),
((1S)-1-((((1S)-1-benzyl-3-(cyclopropylamino)-2,3-dioxo-propyl)amino)carbonyl)-3-methylbutyl)carbamic acid (3S)-tetrahydro-furan-3-yl ester (Compound 5),
((1S)-1-((((1S)-1-benzyl-3-cyclopropylamino-2,3-dioxo-propyl)amino)carbonyl)-3-methylbutyl)carbamic acid tetrahydro-4H-pyran-4-yl ester (Compound 6),
((1S)-1-((((1S)-1-benzyl-2,3-dioxo-3-(propylamino)propyl)amino)carbonyl)-3-methylbutyl)carbamic acid 2-methoxyethyl ester (Compound 7),
((1S)-1-((((1S)-1-benzyl-2,3-dioxo-3-(cyclobutylamino)propyl)amino)carbonyl)-3-methylbutyl)carbamic acid 2-methoxyethyl ester (Compound 8),
((1S)-1-((((1S)-1-benzyl-3-butylamino-2,3-dioxo-propyl)amino)carbonyl)-3-methylbutyl)carbamic acid 2-methoxyethyl ester (Compound 9),
((1S)-1-((((1S)-1-benzyl-2,3-dioxo-3-(2,2,2-trifluoroethylamino)propyl)amino)carbonyl)-3-methylbutyl)carbamic acid 2-methoxyethyl ester (Compound 10),
((1S)-1-((((1S)-1-benzyl-2,3-dioxo-3-(2-indanylamino)propyl)amino)carbonyl)-3-methylbutyl)carbamic acid 2-methoxyethyl ester (Compound 11),
((1S)-1-((((1S)-1-benzyl-2,3-dioxo-3-(2-methoxyethylamino)propyl)amino)carbonyl)-3-methylbutyl)carbamic acid 2-methoxyethyl ester (Compound 12),
((1S)-1-((((1S)-2,3-Dioxo-3-ethylamino-1-(phenylethyl)propyl)amino)carbonyl)-3-methylbutyl)carbamic acid 2-methoxyethyl ester (Compound 13),
((1S)-1-((((1S)-2,3-dioxo-3-ethylamino-1-(phenylethyl)propyl)amino)carbonyl)-3-methylbutyl)carbamic acid (3S)-tetrahydro-furan-3-yl ester (Compound 14),
((1S)-1-((((1S)-2,3-dioxo-3-cyclopropylamino-1-(phenylethyl)propyl)amino)carbonyl)-3-methylbutyl)carbamic acid 2-methoxyethyl ester (Compound 15),
((1S)-1-((((1S)-2,3-dioxo-3-cyclopropylamino-1-(phenylethyl)propyl)amino)carbonyl)-3-methylbutyl)carbamic acid (3S)-tetrahydro-furan-3-yl ester (Compound 16),
((1S)-1-((((1S)-1-benzyl-2,3-dioxo-3-(cyclopropylamino)propyl)amino)carbonyl)-3-methylbutyl)carbamic acid 5-methoxy-3-oxapentyl ester (Compound 17),
((1S)-1-((((1S)-1-benzyl-2,3-dioxo-3-(cyclopropylamino)propyl)amino)carbonyl)-3-methylbutyl)carbamic acid 8-methoxy-3,6-dioxaoctyl ester (Compound 18),
((1S)-1-((((1S)-1-benzyl-2,3-dioxo-3-(cyclopropylamino)propyl)amino)carbonyl)-3-methylbutyl)carbamic acid 11-methoxy-3,6,9-trioxaundecanyl ester (Compound 19),
((1S)-1-((((1S)-1-benzyl-2,3-dioxo-3-(cyclopropylamino)propyl)amino)carbonyl)-3-methylbutyl)carbamic acid 14-methoxy-3,6,9,12-tetraoxa-tetradecanyl ester (Compound 20),
((1S)-1-((((1S)-2,3-dioxo-1-(2-methylpropyl)-3-(2-phenoxyethyl)aminopropyl)amino)carbonyl)-3-methylbutyl)carbamic acid 2-methoxyethyl ester (Compound 21),
((1S)-1-((((1S)-2,3-dioxo-1-(2-methylpropyl)-3-(2-phenoxyethyl)aminopropyl)amino)carbonyl)-3-methylbutyl)carbamic acid 5-methoxy-3-oxa-pentyl ester (Compound 22),
((1S)-1-((((1RS)-3-amino-1-benzyl-2,3-dioxo-propyl)amino)carbonyl)-3-methylbutyl)carbamic acid 5-methoxy-3-oxa-pentyl ester (Compound 23),
((1S)-1-((((1S)-1-benzyl-3-(cyclopropylamino)-2,3-dioxo-propyl)amino)carbonyl)-3-methylbutyl)carbamic acid 2-(pyridin-2-yl)ethyl ester (Compound 24),
((1S)-1-((((1S)-1-benzyl-3-(cyclopropylamino)-2,3-dioxo-propyl)amino)carbonyl)-3-methylbutyl)carbamic acid 2-(6-methylpyridin-2-yl)ethyl ester (Compound 25),
((1S)-1-((((1S)-1-benzyl-3-(cyclopropylamino)-2,3-dioxo-propyl)amino)carbonyl)-3-methylbutyl)carbamic acid 2-(5-ethylpyridin-2-yl)ethyl ester (Compound 26),
((1S)-1-((((1S)-1-benzyl-3-(cyclopropylamino)-2,3-dioxo-propyl)amino)carbonyl)-3-methylbutyl)carbamic acid 2-tert-butoxyethyl ester (Compound 27),
((1S)-1-((((1S)-1-benzyl-3-(cyclopropylamino)-2,3-dioxo-propyl)amino)carbonyl)-3-methylbutyl)carbamic acid 2-isopropoxyethyl ester (Compound 28) and the like, among which compounds 4, 17, 18, 19 and 24 are preferable.

These compounds of the present invention have not yet been reported in literatures, and thus are novel. As shown in Test Examples which will be hereinafter described, the compounds of the present invention have an excellent calpain inhibitory activity. Accordingly, a medicament containing a compound of the present invention as active ingredient, optionally together with a combination of carriers which will be hereinafter described, is useful as a calpain inhibitor.

The medicament containing a compound of the present invention is useful as a prophylactic or therapeutic agent for mammal (e.g. human, rat, mouse, rabbit, cattle, pig, dog, cat) diseases related to calpain such as ischemic disease, immunologic disease, multiple sclerosis, Alzheimer's disease, osteoporosis, diseases caused by brain tissue damage, cataract, glaucoma, retinochoroiditis disease (diabetic retinopathy, retinal vein occulusion, macular degeneration, retinitis pigmentosa, hypertensive retinopathy, retinal detachment, etc.), posterior eyeball complications due to photocoagulation (e.g. macular edema, retinal detachment, optic neuritis, visual field defect, light sense defect, dyschromatopsia, etc.), a disease involving neovascularization or the like.

In addition, a compound of the present invention has excellent tissue transport and high absorbability as well as high safety with very low toxicity.

The medicament containing a compound of the present invention can be administered systemically or locally. Besides oral administration, The systemic administration includes, besides oral administration, parenteral administration route such as intravenous injection, subcutaneous injection, intramuscular injection or the like. In case of the local administration, the medicament is applied via transdermal, mucous membrane, nasal or ophthalmic route, etc.

The dosage form of the medicament containing a compound of the present invention includes solid preparations (e.g. powders, granules, tablets, capsules, suppositories, etc.) and liquid preparations (e.g. syrups, injections, eye drops, nasal drops, etc.). In the production of granules or tablets, any dosage form can be prepared with the use of pharmaceutically acceptable additives such as excipients (e.g. lactose, sucrose, glucose, starch, crystalline cellulose, etc.), lubricants (e.g. magnesium stearate, talc, stearic acid, calcium stearate), disintegrators (e.g. starch, carmellose sodium, calcium carbonate, etc.), or binders (e.g. starch paste, hydroxypropylcellulose solution, carmellose solution, gum arabic solution, gelatin solution, sodium alginate solution, etc.). Further, granules and tablets may be coated with a coating agent (e.g. gelatin, white sugar, gum arabic, carnauba wax, etc.) or an enteric coating agent (e.g. cellulose acetate phthalate, methacrylic copolymer, hydroxypropylcellulose phthalate, carboxymethylethyl cellulose, etc.).

In the production of capsules, conventional excipients such as magnesium stearate, calcium stearate, talc and light silicic acid anhydride, etc., for improving flowability and lubricity; crystalline cellulose and lactose for increasing flowability under pressure; and the above-mentioned disintegrators are appropriately selected, and mixed or granulated homogenously with the compound of the present invention, then filled in capsules. Alternatively, the granulated products may be coated with a suitable coating agent, then filled in capsules, or may be encapsulated with an appropriate capsule base (e.g. glycerin) having increased plasticity endowed with addition of glycerin or sorbitol. If required; coloring agents, preservatives (e.g. sulfur dioxide, parabens such as methyl p-oxybenzoate, ethyl p-oxybenzoate and propyl p-oxybenzoate), etc. may be added to the capsule preparations. Enteric coated capsules, gastric resistant capsules or release controlled capsules may be formulated in addition to conventional capsule preparations. In the case of enteric coated capsule preparations, they are prepared by filling regular capsules with the compound of the present invention which is coated with an enteric coating agent or to which said appropriate excipient is added, or alternatively, they are prepared by filling capsules coated with an enteric coating agent or capsules made from an enteric polymer as a base material with the compound of the present invention optionally together with said appropriate excipient. In the production of suppositories, an appropriate suppository base (e.g. cacao butter, macrogol, etc.) can be used.

In the production of syrups, stabilizers (e.g. sodium edetate, etc.), suspending agents (e.g. gum arabic, carmellose, etc.), corrigents (e.g. simple syrup, glucose, etc.), perfumes or the like can be appropriately used.

Injections, eye-drops or nasal drops of the present invention can be produced by dissolving or dispersing the compound of the present invention in a solution containing an appropriate isotonic (e.g. sodium chloride, potassium chloride, glycerin, mannitol, sorbitol, boric acid, borax, glucose, propylene glycol, etc.), buffer (e.g. phosphate buffer, acetate buffer, borate buffer, carbonate buffer, citrate buffer, Tris buffer, glutamate buffer, $\epsilon$-aminocapronate buffer, etc.), preservative (e.g. methyl p-oxybenzoate, ethyl p-oxybenzoate, propyl p-oxybenzoate, chlorobutanol, benzyl alcohol, benzalkonium chloride, sodium dehydroacetate, sodium edetate, boric acid, borax, etc.), thickener (e.g. hydroxyethylcellulose, hydroxypropylcellulose, polyvinyl alcohol, polyethylene glycol, etc.), stabilizer (e.g. sodium hydrogensulfite, sodium thiosulfate, sodium edetate, sodium citrate, ascorbic acid, dibutylhydroxytoluene, etc.), pH controlling agent (e.g. hydrochloric acid, sodium hydroxide, phosphoric acid, acetic acid, etc.) or the like.

Although the amount of the additive to the above injection, eye drop or nasal drop depends on the kind and the purpose of the additive to be added, it is sufficient to add the amount of the additive that can achieve the purpose. Usually, an isotonic is preferably added in an amount of about 0.5 to about 5.0 w/v % so that the osmotic pressure reaches about 229 mOsm to about 343 mOsm. Preferred concentrations of buffer, thickner and stabilizer to be added are about 0.01 to about 2.0 w/v %, about 0.01 to about 1.0 w/v % and about 0.001 to about 1.0 w/v %, respectively. A pH controlling agent is appropriately added to adjust the pH usually to about 3 to about 9, preferably about 4 to about 8.

The dose of the compound of the present invention depends on the target diseases, symptom of the disease, subject to be administered, administration route or the like. For example, in the case of oral administration to an adult patient, the dose is about 1 to about 200 mg, preferably about 10 to about 100 mg for a single dose, once to several times a day. In the case of injection to an adult patient, the dose is about 0.1 to about 50 mg, preferably about 1 to about 30 mg, once a day. For topical administration to the eyes, it is preferable to administer eye drops containing usually about 0.001 to about 1.0 w/v %, preferably about 0.01 to about 0.5 w/v %, in an amount of about 20 to about 50 µL per dose, several times a day.

EXAMPLES

The present invention will be explained in detail by way of Reference Examples, Examples, Test Examples and Formulation Examples, however, the invention is not restricted thereto.

In the analytical data of the compounds described in the Examples, melting points were determined on a Yanaco micro melting point apparatus without correction. $^1$H-NMR spectra were recorded on a Varian Gemini-2000 spectrometer. Chemical shifts are reported in parts per million, and coupling constants (J) are reported in hertz. Matrix-assisted laser desorption ionization time-of-flight mass spectra (MALDI-TOF-MS) were obtained on a Perseptive Voyager DE mass spectrometer, and the mass numbers were corrected with an internal standard ($\alpha$-cyano-4-hydroxycinnamic acid) and displayed accurately.

Reference Example 1

N-((2-Methoxyethoxy)carbonyl)-L-leucine N-hydroxy-succinimide ester (1) To a solution of L-leucine (25 g, 0.19 mol) was dissolved in 2M NaOH (0.12 L) was slowly added 2-methoxyethyl chloroformate (30 g, 0.22 mol) and 1M NaOH at the same time under the ice-cooled condition. The mixture was stirred at room temperature for 18 hours, diluted into water (600 mL) and washed with ethyl ether (2×200 mL). The aqueous phase was cooled in an ice bath and acidified to pH 3 with 6M HCl. This mixture was extracted with ethyl acetate (EtOAc) (5×150 mL). The organic phase was dried over anhydrous MgSO$_4$ and filtered, and the filtrate was concentrated in vacuo to yield N-((2-methoxyethoxy)carbonyl)-L-leucine (41 g, 92%) as a colorless oil.

(2) N-((2-Methoxyethoxy)carbonyl)-L-leucine (20 g, 86 mmol) and N-hydroxysuccinimide (13 g, 0.11 mmol) were dissolved in THF (200 mL), and a suspension of 1-ethyl-3-(3-dimethylaminopropyl)carbodiimide hydrochloride (21 g, 0.11 mol) in CH$_2$Cl$_2$ (200 mL) was added thereto. The mixture was stirred at room temperature for 18 hours, and concentrated in vacuo. The residue was dissolved in EtOAc (300 mL), and the solution was washed with 1M HCl (150 mL), saturated aqueous NaHCO$_3$ (150 mL) and saturated aqueous NaCl (150 mL), dried over anhydrous MgSO$_4$, and concentrated in vacuo to give the title compound (27 g, 95%) as a colorless oil.

$^1$H-NMR (300 MHz, DMSO-d$_6$) δ0.89 (d, 3H, J=6.6), 0.93 (d, 3H, J=6.6), 1.57-1.84 (m, 3H), 2.81 (s, 4H), 3.26 (s, 3H), 3.51 (t, 2H, J=4.7), 4.10 (t, 2H, J=4.7), 4.40 (m, 1H), 8.04 (d, 1H, J=8.1).

Reference Example 2

(1) N-(((3S)-Tetrahydrofuran-3-yloxy)carbonyl)-L-leucine N-hydroxysuccinimide ester To a stirred solution of (S)-3-hydroxytetrahydrofuran (1.0 g, 11 mmol) in acetonitrile (50 mL) at room temperature were added N,N'-disuccinimidyl carbonate (4.3 g, 17 mmol) and triethylamine (4.4 g, 17 mmol, 4.8 mL). The resulting mixture was stirred at room temperature for 18 hours, and concentrated in vacuo. The residue was diluted with saturated aqueous NaHCO$_3$ (100 mL) and extracted with EtOAc (200 mL). The combined organic extracts were washed with saturated aqueous NaCl (100 mL), dried over anhydrous MgSO$_4$, and concentrated in vacuo to give N-succinimidyl(3S)-3-tetrahydrofranyl carbonate (2.6 g) as a brown oil in a quantitative yield.

(2) To a solution of L-leucine ethyl ester hydrochloride (2.7 g, 14 mmol) and triethylamine (2.9 g, 28 mmol) in dichloromethane (50 mL) was added a solution of N-succinimidyl (3S)-3-tetrahydrofurnaylcarbonate (2.6 g, 11 mmol) in dichloromethane (20 mL), and the mixture was stirred at room temperature for 18 hours, then concentrated in vacuo. The residue was dissolved in ethyl acetate (200 mL), and the solution was washed successively with 1M hydrochloric acid, saturated aqueous NaHCO$_3$ and saturated aqueous NaCl, dried over anhydrous magnesium sulfate, and concentrated in vacuo. The residue was washed with hexane to give N-((((3S)-tetrahydrofuran-3-yloxy)carbonyl)-L-leucine ethyl ester (3.1 g, 98%) as a white solid.

(3) To a solution of N-(((3S)-tetrahydrofuran-3-yloxy)carbonyl)-L-leucine ethyl ester (2.9 g, 11 mmol) in EtOH (100 mL) was added 1M NaOH (33 mL). The mixture was stirred under ice-cooling condition for 3 hours, and then adjusted to pH 3 by the addition of HCl thereto. The solution was concentrated in vacuo, and the residue was extracted with ethyl acetate (100 mL). Then, the organic layer was separated, washed with 1M HCl and saturated aqueous NaCl, dried over anhydrous MgSO$_4$ and concentrated in vacuo. The residue was crystallized from ethyl acetate and hexane to give N-(((3S)-tetrahydrofuran-3-yloxy)carbonyl)-L-leucine (2.6 g, 85%) as colorless crystals.

M.p. 94.9-96.0° C.

(4) Following the reaction in an analogous manner to Reference Example 1(2) and using N-(((3S)-tetrahydrofuran-3-yloxy)carbonyl)-L-leucine in place of N-((2-methoxyethoxy)carbonyl)-L-leucine, there was obtained the title compound as a colorless oil.

$^1$H-NMR(300 MHz, DMSO-d$_6$) δ 60.89 (d, 3H, J=6.0), 0.92 (d, 3H, J=6.3), 1.55-1.82 (m, 3H), 1.88 (m, 1H), 2.12 (m, 1H), 2.81 (s, 4H), 3.64-3.84 (m, 4H), 4.39 (m, 1H), 5.15 (m, 1H), 8.04 (d, 1H, J=7.8).

Reference Example 3

N-((Tetrahydro-4H-pyran-4-yloxy)carbonyl)-L-leucine N-hydroxysuccinimide ester (1) N-Succinimidyl tetrahydro-4H-pyran-4-ylcarbonate was obtained as a brown oil in a manner similar to Reference Example 2(1), using 4-hydroxytetrahydro-4H-pyran in place of (S)-3-hydroxytetrahydrofuran, there was obtained N-succinimidyl tetrahydro-4H-pyran-4-ylcarbonate as a brown oil.

(2) Following the reaction in an analogous manner to Reference Example 2(2) and using N-succinimidyl tetrahydro-4H-pyran-4-ylcarbonate in place of N-succinimidyl (3S)-3-tetrahydrofuranyl carbonate, there was obtained N-((tetrahydro-4H-pyran-4-yloxy)carbonyl)-L-leucine ethyl ester as a colorless solid.

(3) Working up in a manner similar to Reference Example 2(3) and using N-(5-methoxy-3-oxaopentyloxy)carbonyl)-L-leucine ethyl ester in place of N-(((3S)-tetrahydrofuran-3-yloxy)carbonyl)-L-leucine ethyl ester, there was obtained N-((tetrahydro-4H-pyran-4-yloxy)carbonyl)-L-leucine as a colorless solid.

(4) Using N-((tetrahydro-4H-pyran-4-yloxy)carbonyl)-L-leucine) in place of N-(2-(methoxyethoxy)carbonyl)-L-leucine, a similar reaction to Reference Example 1(2) gave the title compound as a colorless oil.

$^1$H-NMR(300 MHz, DMSO-d$_6$) δ 0.89 (d, 3H, J=6.0), 0.92 (d, 3H, J=6.3), 1.43-1.93 (m, 7H), 2.80 (s, 4H), 3.42 (m, 2H), 3.78-3.82 (m, 2H), 4.39 (m, 1H), 4.72 (m, 1H), 7.94 (d, 1H, J=7.8).

Reference Example 4

N-((5-Methoxy-3-oxapentyloxy)carbonyl)-L-leucine N-hydroxysuccinimide ester (1) Following the reaction in an analogous manner to Reference Example 2(1) and using diethylene glycol monomethyl ether in place of (S)-3-hydroxytetrahydrofuran, there was obtained 5-methoxy-3-oxapentyl N-succinimidyl carbonate as a colorless oil.

(2) Following the reaction in an analogous manner to Reference Example 2(2) and using 5-methoxy-3-oxapentyl N-succinimidyl carbonate in place of N-succinimidyl (3S)-3-tetrahydrofuranyl carbonate, there was obtained N-((5-methoxy-3-oxapentyloxy)carbonyl)-L-leucine ethyl ester as a colorless oil.

(3) Following the reaction in an analogous manner to Reference Example 2(3) and using N-((5-methoxy-3-oxapentyloxy)carbonyl)-L-leucine ethyl ester in place of N-(((3S)-tetrahydrofuran-3-yloxycarbonyl)-L-leucine ethyl ester, there was obtained N-((5-methoxy-3-oxapentyloxy)carbonyl)-L-leucine as a colorless oil.

(4) Following the reaction in an analogous manner to Reference Example 1(2) and using N-((5-methoxy-3-oxapentyloxy)carbonyl)-L-leucine in place of N-((2-methoxyethoxy)carbonyl-L-leucine, there was obtained the title compound as a colorless oil.

$^1$H-NMR(300 MHz, DMSO-d$_6$) δ 0.90 (dd, 6H, J=9.5, 6.5), 1.56-1.80 (m, 3H), 2.80 (s, 4H), 3.24 (s, 3H), 3.41-3.46 (m, 2H), 3.50-3.54 (m, 2H), 3.56-3.60 (m, 2H), 4.08-4.11 (m, 2H), 4.39 (m, 1H), 8.05 (d, 1H, J=7.8).

Reference Example 5

N-((8-Methoxy-3,6-dioxaoctyloxy)carbonyl)-L-leucine N-hydroxysuccinimide ester (1) Following the reaction in an analogous manner to Reference Example 2(1) and using triethylene glycol monomethyl ether in place of (S)-3-hydroxytetrahydrofuran, there was obtained 8-methoxy-3,6-dioxaoctyl N-succinimidyl carbonate as a colorless oil.

(2) Following the reaction in an analogous manner to Reference Example 2(2) and using 8-methoxy-3,6-dioxaoctyl N-succinimidyl carbonate in place of N-succinimidyl (3S)-3-tetrahydrofuranyl carbonate, there was obtained N-((8-methoxy-3,6-dioxaoctyloxy)carbonyl)-L-leucine ethyl ester as a colorless oil.

(3) Following the reaction in an analogous manner to Reference Example 2(3) and using N-(8-methoxy-3,6-dioxaoctyloxy)carbonyl)-L-leucine ethyl ester in place of N-(((3S)-tetrahydrofuran-3-yloxy)carbonyl-L-leucine ethyl ester, there was obtained N-((8-methoxy-3,6-dioxaoctyloxy)carbonyl)-L-leucine as a colorless oil.

(4) Following the reaction in an analogous manner to Reference Example 1(2) and using N-((8-methoxy-3,6-dioxaoctyloxy)carbonyl)-L-leucine in place of N-((2-methoxyethoxy)carbonyl)-L-leucine, there was obtained the title compound as a colorless oil.

$^1$H-NMR(300 MHz, DMSO-d$_6$) δ 0.89 (d, 3H, J=6.3), 0.92 (d, 3H, J=6.3), 1.56-1.82 (m, 3H), 2.81 (s, 4H), 3.24 (s, 3H), 3.43 (m, 2H), 3.52 (m, 6H), 3.59 (m, 2H), 4.10 (m, 2H), 4.40 (m, 1H), 8.06 (d, 1H, J=7.8).

Reference Example 6

N-((11-Methoxy-3,6,9-trioxaundecanyloxy)carbonyl)-L-leucine N-hydroxysuccinimide ester (1) Following the reaction in an analogous manner to Reference Example 2(1) and using tetraethylene glycol monomethyl ether in place of (S)-3-hydroxytetrahydrofuran, there was obtained 11-methoxy-3,6,9-trioxaundecanyl N-succinimidyl carbonate as a colorless oil.

(2) Following the reaction in an analogous manner to Reference Example 2(2) and using 11-methoxy-3,6,9-trioxaundecanyl N-succinimidyl carbonate in place of N-succinimidyl(3S)-3-tetrahydrofuranyl carbonate, there was obtained N-((11-methoxy-3,6,9-trioxaundecanyloxy)carbonyl-L-leucine ethyl ester as a colorless oil.

(3) Following the reaction in an analogous manner to Reference Example 2(3) and using N-((11-methoxy-3,6,9-trioxa-undecanyloxy)carbonyl)-L-leucine ethyl ester in place of N-(((3S)-tetrahydrofuran-3-yloxy)carbonyl)-L-leucine ethyl ester, there was obtained N-((11-methoxy-3,6,9-trioxa-undecanyloxy)carbonyl)-L-leucine as a colorless oil.

(4) Following the reaction in an analogous manner to Reference Example 1(2) and using N-((11-methoxy-3,6,9-trioxaundecanyloxy)carbonyl)-L-leucine in place of N-((2-methoxyethoxy)carbonyl)-L-leucine, there was obtained the title compound as a colorless oil.

$^1$H-NMR(300 MHz, DMSO-d$_6$) δ 0.91 (dd, 6H, J=9.3, 6.3), 1.56-1.77 (m, 3H), 2.81 (s, 4H), 3.24 (s, 3H), 3.41-3.44 (m, 2H), 3.49-3.52 (m, 10H), 3.59 (t, 2H, J=4.7), 4.08-4.11 (m, 2H), 4.38 (m, 1H), 8.06 (d, 1H, J=7.8).

Reference Example 7

N-((14-Methoxy-3,6,9,12-tetraoxatetradecanyloxy) carbonyl)-L-leucine N-hydroxysuccinimide ester (1) Following the reaction in an analogous manner to Reference Example 2(1) and using pentaethylene glycol monomethyl ether in place of (S)-3-hydroxytetrahydrofuran, there was obtained 14-methoxy-3,6,9,12-tetraoxa-tetradecanyl N-succinimidyl carbonate as a colorless oil.

(2) Following the reaction in an analogous manner to Reference Example 2(2) and using 14-methoxy-3,6,9,12-tetraoxa-tetradecanyl N-succinimidyl carbonate in place of N-succinimidyl(3S)-3-tetrahydrofuranyl carbonate, there was obtained N-((14-methoxy-3,6,9,12-tetraoxa-tetradecanyloxy)carbonyl)-L-leucine ethyl ester as a colorless oil.

(3) Following the reaction in an analogous manner to Reference Example 2(3) and using N-((14-methoxy-3,6,9,12-tetraoxa-tetradecanyloxy)carbonyl-L-leucine ethyl ester in place of N-(((3S)-tetrahydrofuran-3-yloxy)carbonyl)-L-leucine ethyl ester, there was obtained N-((14-methoxy-3,6,9, 12-tetraoxa-tetradecanyloxy)carbonyl)-L-leucine as a colorless oil.

(4) Following the reaction in an analogous manner to Reference Example 1(2) and using N-((14-methoxy-3,6,9,12-tetraoxa-tetradecanyloxy)carbonyl L-leucine in place of N-((2-methoxyethoxy)carbonyl)-L-leucine, there was obtained the title compound as a colorless oil.

$^1$H-NMR(300 MHz, DMSO-d$_6$) δ 0.89 (d, 3H, J=6.6), 0.92 (d, 3H, J=6.3), 1.57-1.82 (m, 3H), 2.81 (s, 4H), 3.24 (s, 3H), 3.43 (m, 2H), 3.51 (m, 14H), 3.59 (m, 2H), 4.10 (m, 2H), 4.40 (m, 1H), 8.05 (d, 1H, J=7.8).

Reference Example 8

(3S)-3-Amino-N-ethyl-2-hydroxy-4-phenylbutanamide hydrochloride (1) To a solution of L-phenylalaminol (50 g, 66 mmol) in tetrahydrofuran (1.3 L) and water (630 mL), a solution of di-t-butyl dicarbonate (140 g, 0.67 mol) in tetrahydrofuran (500 mL) and 1M NaOH (660 mL) were added slowly at the same time under ice-cooled condition. The mixture was stirred at room temperature for 18 hours, concentrated in vacuo, and diluted with ethyl acetate (EtOAc) (1 L). The solution was washed with 1M HCl, saturated aq. NaHCO3 and saturated aq. NaCl, dried over anhydrous MgSO4, and concentrated in vacuo. The resulting white solid was recrystalized from ethyl acetate/hexane (1:10). The crystal was filtered off to give N-(tert-butoxycarbonyl)-L-phenylalaminol (70 g, 84%) as colorless crystals.

(2) N-(tert-Butoxycarbonyl)-L-phenylalaminol (69 g, 0.28 mol) was dissolved in DMSO (280 mL) and CH$_2$Cl$_2$ (140 mL), and the solution was in an ice-bath. N,N-diisopropylethylamine (106 g, 0.82 mol) and a suspension of purified sulfur trioxide pyridine complex (130 g, 0.82 mol) in DMSO (100 mL) were added thereto. The mixture was stirred for 1 hour under the same condition. The reaction mixture was diluted with EtOAc (1.5 L), and the solution was washed with 1M HCl, saturated aqueous NaHCO₃ and saturated aqueous NaCl, dried over anhydrous MgSO₄, and concentrated in vacuo. The residue was crystallized from a mixture of hexane and EtOAc to give N-(tert-butoxycarbonyl)-L-phenylalaninal (53 g, 77%) as colorless crystals.

(3) N-(tert-Butoxycarbonyl)-L-phenylalaninal (17 g, 67 mmol) was dissolved in MeOH (100 mL) and chilled to 5° C. Sodium bisulfite (7.0 g, 67 mmol) was dissolved in water (150 mL) and chilled to 5° C. The solution was added to the aldehyde solution, and the mixture was stirred at 5° C. for 18 hours. NaCN (4.0 g, 81 mmol) was dissolved in water (100 mL) and added with EtOAc (300 mL) to the above mixture. The reaction solution was stirred at room temperature for 5 hours. The organic layer was collected, dried over anhydrous MgSO4, and concentrated in vacuo to yield the cyanohydrin as a colorless oil. The cyanohydrin was dissolved in 1,4-dioxane (250 mL) and concentrated HCl (250 mL), and 10 mL of anisole was added. The solution was gently refluxed for 18 hours, allowed to cool to room temperature and then concentrated in vacuo to give a brown semi-solid. The residue was dissolved in water (100 mL) and washed with ethyl ether (3×50 mL). The aqueous phase was then placed on a Dowex 50×8-column (100-200 mesh, H⁺ form; 25×1.8 cm). The column was washed with water until the pH 5.5, and eluted with 2M ammonium hydroxide (ca. 1.5 L). The eluent was concentrated in vacuo to yield (3S)-3-amino-2-hydroxy-4-phenylbutanoic acid (12 g, 88%) as a white solid.

(4) (3S)-3-Amino-2-hydroxy-4-phenylbutyric acid (11 g, 56.34 mmol) was dissolved in 1M NaOH (70 mL), and to this solution was added a solution of di-t-butyl dicarbonate (12 g, 57 mmol) in dioxane (70 mL). The mixture was stirred at room temperature for 18 hours while the pH was maintained between 10 and 11 with 1M NaOH. The mixture was diluted with water (600 mL), and washed with diethyl ether (2×200 mL). The aqueous phase was chilled in an ice bath and acidified to pH 2 with 1M HCl. This mixture was extracted with ethyl ether (3×250 mL). The organic phase was dried over anhydrous MgSO₄ and concentrated in vacuo to yield (3S)-3-(tert-butoxycarbonylamino)-2-hydroxy-4-phenylbutanoic acid (12 g, 72%) as a mixture of diastereomer which was a colorless solid.

(5)(3S)-3-(tert-Butoxycarbonylamino)-2-hydroxy-4-phenylbutanoic acid (6.3 g, 21 mmol) and 1-hydroxybenzotriazole (HOBt) (3.0 g, 22.4 mmol) were dissolved in DMF (45 mL) and cooled in an ice bath. 1-Ethyl-3-(3-dimethylaminopropyl)carbodiimide hydrochloride (EDC) (4.6 g, 24 mmol) was added, followed by aqueous ethylamine solution (3.0 mL). The solution was stirred for 18 hours. The solution was diluted into EtOAc (200 mL) and washed with 1M HCl, saturated aqueous NaHCO3, and saturated aqueous NaCl. The organic layer was dried over anhydrous MgSO₄ and concentrated in vacuo to yield ((1S)-1-benzyl-3-ethylamino-2-hydroxy-3-oxo-propyl)carbamic acid 1,1-dimethylethyl ester (5.8 g, 84%) as a white solid.

(6)((1S)-1-Benzyl-3-ethylamino-2-hydroxy-3-oxopropyl) carbamic acid 1,1-dimethylethyl ester (5.5 g, 17 mmol) was dissolved in 4N HCl/dioxane (65 mL) and was stirred for 3 hours at room temperature. The solution was concentrated in vacuo to yield the title compound as a white solid (4.4 g) in a quantitative yield.

M.p. 162.8-163.3° C.

(Major)¹H-NMR (300 MHz, DMSO-d₆) δ 1.02 (t, 3H, J=7.2), 2.93 (m, 2H), 3.05-3.20 (m, 2H), 3.60 (m, 1H), 3.88 (m, 1H), 6.75 (d, 1H, J=6.0), 7.19-7.37 (m, 5H), 8.08 (m, 1H), 8.17 (br s, 3H).

(Minor)¹H-NMR (300 MHz, DMSO-d₆) δ 0.97 (t, 3H, J=7.4), 2.80 (d, 2H, J=6.9), 3.00 (m, 2H), 3.69 (m, 1H), 4.26 (m, 1H), 6.53 (d, 1H, J=5.4), 7.19-7.37 (m, 5H), 8.03 (t, 1H, J=5.7), 8.17 (br s, 3H).

Reference Example 9

(3S)-3-Amino-N-cyclopropyl-2-hydroxy-4-phenylbutanamide hydrochloride

Following the reaction in an analogous manner to Reference Example 8(5) and using cyclopropylamine in place of aqueous ethylamine, there was obtained ((1S)-1-benzyl-3-cyclopropylamino-2-hydroxy-3-oxopropyl)carbamic acid 1,1-dimethylethyl ester as a white solid.

Following the reaction in an analogous manner to Reference Example 8(6) and using ((1S)-1-benzyl-3-cyclopropylamino-2-hydroxy-3-oxopropyl)carbamic acid 1,1-dimethyl ester in place of ((1S)-1-benzyl-3-ethylamino-2-hydroxy-3-oxopropyl)carbamic acid 1,1-dimethyl ethyl ester, there was obtained the title compound as a white solid.

M.p. 162.9-163.3° C.

¹H-NMR (300 MHz, DMSO-d₆) δ 0.44 (m, 2H), 0.57 (m, 2H), 2.50 (m, 0.5H), 2.65 (m, 0.5H), 2.82 (d, 1H, J=6.9), 2.94 (m, 1H), 3.60 (m, 0.5H), 3.70 (m, 0.5H), 3.87 (m, 0.5H), 4.26 (d, 0.5H, J=2.4), 6.45 (br s, 0.5H), 6.69 (br s, 0.5H), 7.23-7.35 (m, 5H), 7.99 (d, 0.5H, J=4.2), 8.08 (br s, 1.5H), 8.09 (d, 0.5H, J=4.5), 8.23 (br s, 1.5H).

Reference Example 10

(3S)-3-Amino-2-hydroxy-4-phenyl-N-propylbutanamide hydrochloride

Following the reaction in an analogous manner to Reference Example 8(5) and using propylamine in place of aqueous ethylamine, there was obtained ((1S)-1-benzyl-2-hydroxy-3-oxo-3-(propylamino)propyl)carbamic acid 1,1-dimethylethyl ester as a white solid.

Following the reaction in an analogous manner to Reference Example 8(6) and using ((1S)-1-benzyl-2-hydroxy-3-oxo-3-(propylamino)propyl)carbamic acid 1,1-dimethylethyl ester in place of ((1S)-1-benzyl-3-ethylamino-2-hydroxy-3-oxopropyl)carbamic acid 1,1-dimethylethyl ester, there was obtained the title compound as a white solid.

M.p. 127.8-129.5° C.

¹H-NMR (300 MHz, DMSO-d₆) δ 0.82 (m, 3H), 1.35-1.47 (m, 2H), 2.82 (m, 0.5H), 2.95 (m, 3H), 3.09 (m, 0.5H), 3.58 (m, 0.5H), 3.70 (m, 0.5H), 3.92 (m, 0.5H), 4.31 (m, 0.5H), 6.55 (d, 0.5H, J=4.8), 6.77 (d, 0.5H, J=6.6), 7.21-7.36 (m, 5H), 7.98-8.15 (m, 2.5H), 8.24 (br s, 1.5H).

Reference Example 11

(3S)-3-Amino-N-cyclobutyl-2-hydroxy-4-phenylbutanamide hydrochloride

Following the reaction in an analogous manner to Reference Example 8(5) and using cyclobutylamine in place of aqueous ethylamine, there was obtained ((1S)-1-benzyl-3-cyclobutylamino-2-hydroxy-3-oxopropyl)carbamic acid 1,1-dimethylethyl ester as a white solid.

Following the reaction in an analogous manner to Reference Example 8(6) and using ((1S)-1-benzyl-3-cyclobutylamino-2-hydroxy-3-oxopropyl)carbamic acid 1,1-dimethylethyl ester in place of ((1S)-1-benzyl-3-ethylamino-2- hydroxy-3-oxopropyl)carbamic acid 1,1-dimethylethyl ester, there was obtained the title compound as a white solid.

M.p. 162.5-163° C.

$^1$H-NMR (300 MHz, DMSO-d$_6$) δ 1.59 (m, 2H), 1.88-2.18 (m, 4H), 2.80 (d, 1H, J=6.6), 2.91 (m, 1H), 3.58 (m, 0.5H), 3.69 (m, 0.5H), 3.87 (m, 0.5H), 4.08 (m, 0.5H), 4.16-4.24 (m, 1H), 6.50 (d, 0.5H, J=5.4), 6.72 (d, 0.5H, J=6.0), 7.21-7.33 (m, 5H), 8.05 (br s, 1.5H), 8.19 (d, 0.5H, J=7.8), 8.20 (br s, 1.5H), 8.29 (d, 0.5H, J=8.1).

Reference Example 12

(3S)-3-Amino-N-butyl-2-hydroxy-4-phenyl-butanamide hydrochloride

Following the reaction in an analogous manner to Reference Example 8(5) and using butylamine in place of aqueous ethylamine, there was obtained ((1S)-1-benzyl-3-butylamino-2-hydroxy-3-oxopropyl)carbamic acid 1,1-dimethylethyl ester as a white solid.

Following the reaction in an analogous manner, to Reference Example 8(6) and using ((1S)-1-benzyl-3-butylamino-2-hydroxy-3-oxopropyl)carbamic acid 1,1-dimethylethyl ester in place of ((1S)-1-benzyl-3-ethylamino-2-hydroxy-3-oxopropyl)carbamic acid 1,1-dimethylethyl ester, there was obtained the title compound as a white solid.

M.p. 141.0-141.4° C.

$^1$H-NMR (300 MHz, DMSO-d$_6$) δ 0.86 (m, 3H), 1.16-1.47 (m, 4H), 2.80 (m, 0.5H), 2.99 (m, 3H), 3.13 (m, 0.5H), 3.57 (m, 0.5H), 3.70 (m, 0.5H), 3.92 (m, 0.5H), 4.30 (m, 0.5H), 6.53 (br s, 0.5H), 6.77 (d, 0.5H, J=6.6), 7.19-7.39 (m, 5H), 7.97-8.15 (m, 2.5H), 8.22 (s, 1.5H).

Reference Example 13

(3S)-3-Amino-2-hydroxy-4-phenyl-N-(2,2,2-trifluoroethyl)butanamide hydrochloride Following the reaction in an analogous manner to Reference Example 8(5) and using 2,2,2-trifluoroethylamine in place of aqueous ethylamine, there was obtained ((1S)-1-benzyl-2-hydroxy-3-oxo-3-(2,2,2-trifluoroethylamino)propyl)carbamic acid 1,1-dimethylethyl ester as a white solid.

Following the reaction in an analogous manner to Reference Example 8(6) and using ((1S)-1-benzyl-2-hydroxy-3-oxo-3-(2,2,2-trifluoroethylamino)propyl)carbamic acid 1,1-dimethylethyl ester in place of (((1S)-1-benzyl-3-ethylamino-2-hydroxy-3-oxopropyl)carbamic acid 1,1-dimethylethyl ester, there was obtained (3S)-3-amino-2-hydroxy-4-phenyl-N-(2,2,2-trifluoroethyl)butanamide hydrochloride as a white solid.

M.p. 103.0-108.5° C.

$^1$H-NMR (300 MHz, DMSO-d$_6$) δ 2.71-2.85 (m, 1H), 2.88-2.97 (m, 1H), 3.60-3.82 (m, 2.5H), 3.91-4.05 (m, 1H), 4.45 (m, 0.5H), 6.75 (d, 0.5H, J=5.7), 6.98 (d, 0.5H, J=6.3), 7.20-7.35 (m, 5H), 8.12 (br s, 1.5H), 8.25 (br s, 1.5H), 8.70 (m, 1H).

Reference Example 14

(3S)-3-Amino-2-hydroxy-N-(2-indanyl)-4-phenylbutanamide hydrochloride

Following the reaction in an analogous manner to Reference Example 8(5) and using 2-aminoindane in place of aqueous ethylamine, there was obtained ((1S)-1-benzyl-3-(2-indanylamino)-2-hydroxy-3-oxo-propyl)carbamic acid 1,1-dimethylethyl ester as a white solid.

Following the reaction in an analogous manner to Reference Example 8(6) and using ((1S)-1-benzyl-3-(2-indanylamino)-2-hydroxy-3-oxopropyl)carbamic acid 1,1-dimethylethyl ester in place of ((1S)-1-benzyl-3-ethylamino-2-hydroxy-3-oxo-propyl)carbamic acid 1,1-dimethylethyl ester, there was obtained (3S)-3-amino-2-hydroxy-N-(2-indanyl)-4-phenylbutanamide hydrochloride as a white solid.

M.p. 183.0-184.8° C.

$^1$H-NMR (300 MHz, DMSO-d$_6$) δ 2.76-2.96 (m, 4H), 3.01-3.18 (m, 2H), 3.62 (m, 0.5H), 3.74 (m, 0.5H), 3.92 (m, 0.5H), 4.25-4.39 (m, 1H), 4.49 (m, 0.5H), 6.48 (d, 0.5H, J=5.7), 6.72 (d, 0.5H, J=5.7), 7.13-7.35 (m, 9H), 8.15 (m, 3.5H), 8.26 (d, 0.5H, J=7.2).

Reference Example 15

(3S)-3-Amino-2-hydroxy-N-(2-methoxyethyl)-4-phenylbutanamide hydrochloride

Following the reaction in an analogous manner to Reference Example 8(5) and using methoxyethylamine in place of aqueous ethylamine, there was obtained ((1S)-1-benzyl-2-hydroxy-3-(2-methoxyethyl)-3-oxopropyl)carbamic acid 1,1-dimethylethyl ester as a white solid.

Following the reaction in an analogous manner to Reference Example 8(6) and using ((1S)-1-benzyl-2-hydroxy-3-(2-methoxyethyl)-3-oxopropyl)carbamic acid 1,1-dimethylethyl ester in place of ((1S)-1-benzyl-3-ethylamino-2-hydroxy-3-oxopropyl)carbamic acid 1,1-dimethylethyl ester, there was obtained ((3S)-3-amino-2-hydroxy-N-(2-methoxyethyl)-4-phenylbutanamide hydrochloride as a white solid.

M.p. 113.9-117.7° C.

$^1$H-NMR (300 MHz, DMSO-d$_6$) δ 2.82 (d, 1H, J=6.6), 2.95 (m, 1H), 3.10-3.19 (m, 2H), 3.22 (s, 1.5H), 3.23 (s, 1.5H), 3.28-3.34 (m, 2H), 3.57 (m, 0.5H), 3.70 (m, 0.5H), 3.92 (m, 0.5H), 4.32 (m, 0.5H), 6.59 (d, 0.5H, J=4.5), 6.87 (d, 0.5H, J=6.0), 7.22-7.36 (m, 5H), 7.92 t, 0.5H, J=5.7), 7.98 (t, 0.5H, J=5.1), 8.09 (br s, 1.5H), 8.24 (br s, 1.5H).

Reference Example 16

(3S)-3-Amino-N-ethyl-2-hydroxy-5-phenylpentanamide hydrochloride (1) To a solution of Boc-L-homophenylalanine (20 g, 72 mmol) in dimethoxyethane (100 mL) were added N-methylmorpholine (7.2 g, 72 mmol) and isobutyl chloroformate (9.8 g, 72 mmol) in an ice-salt bath. After 1 hour with stirring, the reaction mixture was filtered and the filtrate was cooled in an ice-salt bath, and a solution of NaBH$_4$ (4.1 g, 107 mmol) in water (10 mL) was added, followed by water (300 mL). The resultant precipitates were collected by filtration, and the residue was washed with water and methanol to give N-(tert-butoxycarbonyl)-L-homo-phenylalaminol (15 g, 79%) as colorless crystals.

(2) Following the reaction in an analogous manner to Reference Example 8(2) and using N-(tert-butoxycarbonyl)-L-homophenylalaninol in place of N-(tert-butoxycarbonyl)-L-phenylalaminol, there was obtained N-(tert-butoxycarbonyl)-L-phenylalaninal as a colorless oil.

(3) Following the reaction in an analogous manner to Reference Example 8(3) and using N-(tert-butoxycarbonyl)-L-homophenylalaninal in place of N-(tert-butoxycarbonyl)-L- homophenylalaninal, there was obtained (3S)-3-amino-2-hydroxy-5-phenylpentanoic acid as a white solid.

(4) Following the reaction in an analogous manner to Reference Example 8(4) and using (3S)-3-amino-2-hydroxy-5-phenylpentanoic acid in place of (3S)-3-amino-2-hydroxy-4-phenylbutyric acid, there was obtained (3S)-3-(tert-butoxycarbonylamino)-2-hydroxy-5-phenylpentanoic acid as a colorless oil.

(5) Following the reaction in an analogous manner to Reference Example 8(5) and using (3S)-3-(tert-butoxycarbonylamino)-2-hydroxy-5-phenylpentanoic acid in place of (3S)-3-(tert-butoxycarbonylamino)-2-hydroxy-4-phenylbutanoic acid, there was obtained ((1S)-3-ethylamino-2-hydroxy-3-oxo-1-(phenylethyl)propyl)carbamic acid 1,1-dimethylethyl ester as a white solid.

(6) Following the reaction in an analogous manner to Reference Example 8(6) and using (1S)-3-ethylamino-2-hydroxy-3-oxo-1-(phenylethyl)propyl)carbamic acid 1,1-dimethylethyl ester in place of ((1S)-1-benzyl-3-ethylamino-2-hydroxy-3-oxopropyl)carbamic acid 1,1-dimethylethyl ester, there was obtained (3S)-3-amino-N-ethyl-2-hydroxy-5-phenylpentanamide hydrochloride as a white solid.

M.p. 134.4-134.9° C.

$^1$H-NMR (300 MHz, DMSO-$d_6$) δ 0.99-1.06 (m, 3H), 1.65-1.96 (m, 2H), 2.54-2.76 (m, 2H), 3.07-3.23 (m, 2H), 4.15 (br s, 0.5H), 4.25 (br s, 0.5H), 6.44 (br s, 0.5H), 6.55 (br s, 0.5H), 7.17-7.33 (m, 5H), 7.99 (br s, 1.5H), 8.15 (t, 1H, J=6.2), 8.23 (br s, 1.5H).

Reference Example 17

(3S)-3-Amino-N-cyclopropyl-2-hydroxy-5-phenyl-pentanamide hydrochloride

Following the reaction in an analogous manner to Reference Example 16(5) and using cyclopropylamine in place of aqueous ethylamine, there was obtained ((1S)-3-cyclopropylamino-2-hydroxy-3-oxo-1-(phenylethyl)propyl)carbamic acid 1,1-dimethylethyl ester as a white solid.

Following the reaction in an analogous manner to Reference Example 16(6) and using ((1S)-3-cyclopropylamino-2-hydroxy-3-oxo-1-(phenylethyl)propyl)carbamic acid 1,1-dimethylethyl ester in place of ((1S)-1-benzyl-3-ethylamino-2-hydroxy-3-oxopropyl)carbamic acid 1,1-dimethylethyl ester, there was obtained (3S)-3-amino-N-cyclopropyl-2-hydroxy-5-phenylpentanamide hydrochloride as a white solid.

M.p. 140.2-141.3° C.

$^1$H-NMR (300 MHz, DMSO-$d_6$) δ 0.46-0.64 (m, 4H), 1.64-1.99 (m, 2H), 2.54-2.78 (m, 3H), 3.35 (m, 1H), 4.13 (br s, 0.5H), 4.26 (br s, 0.5H), 6.37 (br s, 0.5H), 6.51 (br s, 0.5H), 7.17-7.33 (m, 5H), 8.05 (br s, 1.5H), 8.15 (d, 0.5H, J=4.5), 8.20 (d, 0.5H, J=4.8), 8.27 (br s, 1.5H).

Reference Example 18

(3S)-3-Amino-2-hydroxy-5-methyl-N-(2-phenoxy-ethyl)-hexanamide hydrochloride (1) Following the reaction in an analogous manner to Reference Example 8(1) and using L-leucinol in place of L-phenylalaminol, there was obtained N-(tert-butoxycarbonyl)-L-leucinol (70 g, 84%) as a colorless oil.

(2) Following the reaction in an analogous manner to Reference Example 8(2) and using N-(tert-butoxycarbonyl)-L-leucinol in place of N-(tert-butoxycarbonyl)-L-phenylalaminol, there was obtained N-(tert-butoxycarbonyl)-L-leucinal as a colorless oil.

(3) Following the reaction in an analogous manner to Reference Examples 8(3) and 8(4) and using N-(tert-butoxycarbonyl)-L-leucinal in place of N-(tert-butoxycarbonyl)-L-phenylalaninal, there was obtained (3S)-3-(tert-butoxycarbonylamino)-2-hydroxy-5-methylhexanoic acid as a colorless oil.

(4) Following the reaction in an analogous manner to Reference Example 8(5) and using (3S)-3-(tert-butoxycarbonylamino)-2-hydroxy-5-methylhexanoic acid in place of (3S)-3-(tert-butoxycarbonylamino)-2-hydroxy-4-phenylbutanoic acid, and 2-phenoxcyethylamine in place of aqueous ethylamine, there was obtained ((1S)-2-hydroxy-1-(2-methylpropyl)-3-oxo-3-(2-phenoxyethyl)amino-propyl)carbamic acid 1,1-dimethylethyl ester as a colorless oil.

(5) Following the reaction in an analogous manner to Reference Example 8(6) and using ((1S)-2-hydroxy-1-(2-methylpropyl)-3-oxo-3-(2-phenoxyethyl)aminopropyl)carbamic acid 1,1-dimethylethyl ester in place of ((1S)-1-benzyl-3-ethylamino-2-hydroxy-3-oxopropyl)carbamic acid 1,1-dimethylethyl ester, there was obtained the title compound as a white solid.

M.p. 93.6-96.2° C.

$^1$H-NMR (300 MHz, DMSO-$d_6$) δ 0.71-0.89 (m, 6H), 1.35-1.47 (m, 2H), 1.72 (m, 1H), 3.48-3.54 (m, 4H), 4.00-4.07 (m, 2H), 4.12 (d, 0.5H, J=3.6), 4.33 (d, 0.5H, J=1.8), 6.91-6.96 (m, 3H), 7.27-7.32 (m, 2H), 7.95(br s, 1.5H), 8.19-8.29(m, 2.5H).

Reference Example 19

3-Amino-2-hydroxy-5-phenylpentanamide hydrochloride

Following the reaction in an analogous manner to Reference Example 8(5) and using ammonia gas in place of aqueous ethylamine, there was obtained 1-benzyl-3-amino-2-hydroxy-3-oxopropyl)carbamic acid 1,1-dimethylethyl ester as a white solid.

Following the reaction in an analogous manner to Reference Example 8(6) and using (1-benzyl-3-amiino-2-hydroxy-3-oxopropyl)carbamic acid 1,1-dimethylethyl ester in place of ((1S)-1-benzyl-3-ethylamino-2-hydroxy-3-oxo-propyl)carbamic acid 1,1-dimethylethyl ester, there was obtained the title compound as a white solid.

$^1$H-NMR (300 MHz, DMSO-$d_6$) δ 2.82 (m, 1H), 2.93 (m, 1H), 3.61 (m, 1H), 3.85 (m, 0.5H), 4.26 (m, 0.5H), 6.48 (d, 0.5H, J=4.8), 6.75 (d, 0.5H, J=5.7), 7.24-7.35 (m, 5H), 7.52 (m, 2H), 8.04 (br s, 1.5H), 8.17 (br s, 1.5H).

Reference Example 20

N-((2-(Pyridine-2-yl)ethyl)carbonyl)-L-leucine N-hydroxysuccinimide ester (1) Following the reaction in an analogous manner to Reference Example 2(1) and using (2-pyridyl)ethanol in place of (S)-3-hydroxytetrahydrofuran, there was obtained N-succinimidyl 2-(pyridin-2-yl)ethylcarbonate as a brown oil.

(2) Following the reaction in an analogous manner to Reference Example 2(2) and using N-succinimidyl 2-(pyridin-2-yl)ethylcarbonate in place of N-succinimidyl (3S)-3-tetrahydrofuranyl carbonate, there was obtained N-((2-(pyridin-2-yl)ethyloxy)carbonyl)-L-leucine ethyl ester as a colorless oil.

(3) Following the reaction in an analogous manner to Reference Example 2(3) and using N-((2-(pyridin-2-yl)ethyloxy)carbonyl)-L-leucine ethyl ester in place of N-(((S)-tetrahydrofuran-3-yloxy)carbonyl)-L-leucine ethyl ester, there was obtained N-((2-(pyridin-2-yl)ethyloxy)carbonyl)-L-leucine as a white solid.

(4) Following the reaction in an analogous manner to Reference Example 1(2) and using N-((2-(pyridin-2-yl)ethyloxy)carbonyl)-L-leucine in place of N-((2-methoxyethoxy)carbonyl-L-leucine, there was obtained the title compound as a colorless oil.

$^1$H-NMR (300 MHz, DMSO-d$_6$) δ 0.82-0.91 (m, 6H), 1.42-1.76 (m, 3H), 2.76-2.81 (m, 4H), 3.00-3.06 (m, 2H), 4.30-4.40 (m, 3H), 7.23 (dd, 1H, J=7.1, 5.3), 7.30 (d, 1H, J=7.8), 7.71 (m, 1H), 7.90 (d, 1H, J=8.1), 8.50 (d, 1H, J=4.5).

Reference Example 21

N-((2-(6-Methylpyridin-2-yl)ethyloxy)carbonyl)-L-leucine N-hydroxysuccinimide ester (1) Following the reaction in an analogous manner to Reference Example 2(1) and using 2-(6-methylpyridin-2-yl)ethanol in place of (S)-3-hydroxytetrahydrofuran, there was obtained N-succinimidyl 2-(6-methylpyridin-2-yl)ethylcarbonate as a brown oil.

(2) Following the reaction in an analogous manner to Reference Example 2(2) and using N-succinimidyl 2-(6-methylpyridin-2-yl)ethylcarbonate in place of N-succinimidyl (3S)-3-tetrahydrofuranyl carbonate, there was obtained N-((2-(6-methylpyridin-2-yl)ethyloxy)carbonyl)-L-leucine ethyl ester as a colorless oil.

(3) Following the reaction in an analogous manner to Reference Example 2(3) and using N-((2-(6-methylpyridin-2-yl)ethyloxy)carbonyl)-L-leucine ethyl ester in place of N-(((3S)-tetrahydrofuran-3-yloxy)carbonyl)-L-leucine ethyl ester, there was obtained N-((2-(6-methylpyridin-2-yl)ethyloxy)carbonyl)-L-leucine as a colorless oil.

(4) Following the reaction in an analogous manner to Reference Example 1(2) and using N-((2-(6-methylpyridin-2-yl)ethyloxy)carbonyl)-L-leucine in place of N-((2-methoxyethoxy)carbonyl)-L-leucine, there was obtained the title compound as a colorless oil.

$^1$H-NMR (300 MHz, DMSO-d$_6$) δ 0.83-0.92 (m, 6H), 1.49-1.77 (m, 3H), 2.43 (s, 3H), 2.81 (s, 4H), 2.99 (t, 2H, J=6.5), 4.29-4.42 (m, 3H), 7.07-7.09 (m, 2H), 7.58 (t, 1H, J=7.7), 7.91 (d, 1H, J=8.4).

Reference Example 22

N-((2-(5-Ethylpyridin-2-yl)ethyloxy)carbonyl)-L-leucine N-hydroxysuccinimide ester (1) Following the reaction in an analogous manner to Reference Example 2(1) and using (5-ethylpyridin-2-yl)ethanol in place of (S)-3-hydroxytetrahydrofuran, there was obtained N-succinimidyl 2-(5-ethylpyridin-2-yl)ethylcarbonate as a brown oil.

(2) Following the reaction in an analogous manner to Reference Example 2(2) and using N-succinimidyl 2-(5-ethylpyridin-2-yl)ethylcarbonate in place of N-succinimidyl (3S)-3-tetrahydrofuranyl carbonate, there was obtained N-((2-(5-ethylpyridin-2-yl)ethyloxy)carbonyl)-L-leucine ethyl ester as a colorless oil.

(3) Following the reaction in an analogous manner to Reference Example 2(3) and using N-(((2-(5-ethylpyridin-2-yl)ethyloxy)carbonyl)-L-leucine ethyl ester in place of N-(((3S)-tetrahydrofuran-3-yloxy)carbonyl)-L-leucine ethyl ester, there was obtained N-((2-(5-ethylpyridin-2-yl)ethyloxy)carbonyl)-L-leucine as a colorless oil.

(4) Following the reaction in an analogous manner to Reference Example 1(2) and using N-((2-(5-ethylpyridin-2-yl)ethyloxy)carbonyl)-L-leucine in place of N-((2-methoxyethoxy)carbonyl)-L-leucine, there was obtained the title compound as a colorless oil.

$^1$H-NMR (300 MHz, DMSO-d$_6$) δ 0.75-0.92 (m, 6H), 1.12-1.25 (m, 3H), 1.36-1.72 (m, 3H), 2.54-2.63 (m, 2H), 2.81-2.83 (m, 4H), 2.96-3.02 (m, 2H), 4.04 (m, 1H), 4.29-4.37 (m, 2H), 7.21 (d, 1H, J=7.8), 7.53 (m, 1H), 7.90 (d, 1H, J=7.8), 8.34 (m, 1H).

Reference Example 23

N-((2-tert-Butdxyethyloxy)carbonyl)-L-leucine N-hydroxysuccinimide ester (1) Following the reaction in an analogous manner to Reference Example 2(1) and using ethylene glycol tert-butyl ether in place of (S)-3-hydroxytetrahydrofuran, there was obtained N-succinimidyl 2-tert-butoxyethyl carbonate as a colorless oil.

(2) Following the reaction in an analogous manner to Reference Example 2(2) and using N-succinimidyl 2-tert-butoxyethyl carbonate in place of N-succinimidyl (3S)-3-tetrahydrofuranyl carbonate, there was obtained N-((2-tert-butoxyethyloxy)carbonyl)-L-leucine ethyl ester as a colorless oil.

(3) Following the reaction in an analogous manner to Reference Example 2(3) and using N-((2-tert-butoxyethyloxy)carbonyl)-L-leucine ethyl ester in place of N-(((3S)-tetrahydrofuran-3-yloxy)carbonyl)-L-leucine ethyl ester, there was obtained N-((2-tert-butoxyethyloxy)carbonyl)-L-leucine as a colorless oil.

(4) Following the reaction in an analogous manner to Reference Example 1(2) and using N-((2-tert-butoxyethyloxy)carbonyl)-L-leucine in place of N-((2-methoxyethyloxy)carbonyl)-L-leucine, there was obtained the title compound as a colorless oil.

$^1$H-NMR (300 MHz, DMSO-d$_6$) δ 0.89 (d, 3H, J=6.3), 0.92 (d, 3H, J=6.3), 1.13 (s, 9H), 1.61 (m, 1H), 1.74 (m, 2H), 2.81 (s, 4H), 3.48 (t, 2H, J=4.7), 4.04 (m, 2H), 4.40 (m, 1H), 8.00 (d, 1H, J=7.8).

Reference Example 24

N-((2-Isopropoxyethyloxy)carbonyl)-L-leucine N-hydroxysuccinimide ester (1) Following the reaction in an analogous manner to Reference Example 2(1) and using ethylene glycol isopropyl ether in place of (S)-3-hydroxytetrahydrofuran, there was obtained N-succinimidyl 2-isopropoxyethyl carbonate as a colorless oil.

(2) Following the reaction in an analogous manner to Reference Example 2(2) and using N-succinimidyl 2-isopropoxyethyl carbonate in place of N-succinimidyl (3S)-3-tetrahydrofuranyl carbonate, there was obtained N-((2-isopropoxyethyloxy)carbonyl)-L-leucine ethyl ester as a colorless oil.

(3) Following the reaction in an analogous manner to Reference Example 2(3) and using N-((2-isopropoxyethyloxy)carbonyl)-L-leucine ethyl ester in place of N-(((3S)-tetrahydrofuran-3-yloxy)carbonyl)-L-leucine ethyl ester, there was obtained N-((2-isopropoxyethyloxy)carbonyl)-L-leucine as a colorless oil.

(4) Following the reaction in an analogous manner to Reference Example 1(2) and using N-((2-isopropoxyethyloxy)

carbonyl)-L-leucine in place of N-((2-methoxyethyloxy)carbonyl)-L-leucine, there was obtained the title compound as a colorless oil.

$^1$H-NMR (300 MHz, DMSO-$d_6$) δ 0.89 (d, 3H, J=6.6), 0.92 (d, 3H, J=6.3), 1.08 (d, 6H, J=6.3), 1.61 (m, 1H), 1.74 (m, 2H), 2.81 (s, 4H), 3.53 (m, 2H), 3.57 (m, 1H), 4.07 (m, 2H), 4.40 (m, 1H), 8.02 (d, 1H, J=7.8).

Example 1

((1S)-1-((((1S)-1-Benzyl-2,3-dioxo-3-(ethylamino)propyl)amino)carbonyl)-3-methylbutyl)carbamic acid 2-methoxyethyl ester (Compound 1)

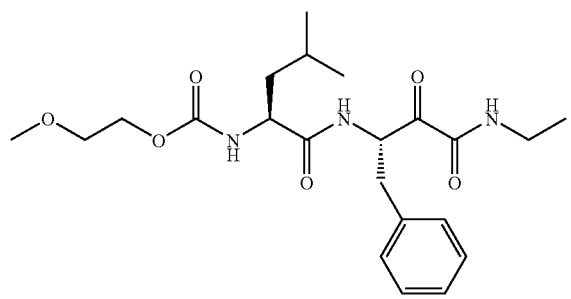

To a solution of the compound of Reference Example 1 (1.2 g, 3.6 mmol) and the compound of Reference Example 8 (1.0 g, 4.0 mmol) in DMF was added triethylamine (1.1 g, 11 mmol, 1.5 mL). The mixture was stirred at room temperature for 18 hours, and concentrated in vacuo. The residue was dissolved in ethyl acetate (EtOAc), and the solution was washed with 1M HCl, saturated aqueous NaHCO$_3$ and saturated aqueous NaCl, dried over anhydrous MgSO$_4$, and concentrated in vacuo. The resulting white solid was washed with a mixture of EtOAc and hexane (1:9) to give ((1S)-1-((((1S)-1-benzyl-3-ethylamino-2-hydroxy-3-oxopropyl)amino)carbonyl)-3-methylbutyl)carbamic acid 2-methoxyethyl ester (0.75 g, 47%) as a white solid.

To a solution of ((1S)-1-((((1S)-1-benzyl-3-ethylamino-2-hydroxy-3-oxo-propyl)amino)carbonyl)-3-methylbutyl)carbamic acid 2-methoxyethyl ester (0.7 g, 1.6 mmol) in CH$_2$Cl$_2$ (70 mL) was added Dess-Martin periodinane (1.0 g, 2.4 mmol). The mixture was stirred at room temperature for 18 hours. Aqueous 10% Na$_2$S$_2$O$_3$ (35 mL) and saturated aqueous NaHCO$_3$ (35 mL) were added thereto, and the mixture was stirred at room temperature for 30 minutes. The organic layer was separated, washed with 1M HCl, saturated aqueous NaHCO$_3$ and saturated aqueous NaCl, dried over MgSO$_4$, and concentrated in vacuo. The residue was crystallized from EtOAc/hexane to give the title compound (0.62 g, 88%) as colorless crystals. M.p. 138.0-138.3° C.

$^1$H-NMR (300 MHz, DMSO-$d_6$) δ 0.83 (d, 3H, J=7.5), 0.85 (d, 3H, J=7.2), 1.04 (t, 3H, J=7.1), 1.35 (m, 2H), 1.56 (m, 1H), 2.82 (m, 1H), 3.14 (m, 3H), 3.25 (s, 3H), 3.47 (t, 2H, J=4.5), 4.04 (m, 3H), 5.19 (m, 1H), 7.16-7.33 (m, 6H), 8.24 (d, 1H, J=7.2), 8.70 (m, 1H).

MALDI-TOF-MS calcd for $C_{22}H_{33}N_3O_6$ (M+Na)$^+$, 458.2267. Found: 458.2361.

Example 2

((1S)-1-((((1S)-1-Benzyl-2,3-dioxo-3-(ethylamino)propyl)amino)carbonyl)-3-methylbutyl)carbamic acid (3S)-tetrahydrofuran-3-yl ester (Compound 2)

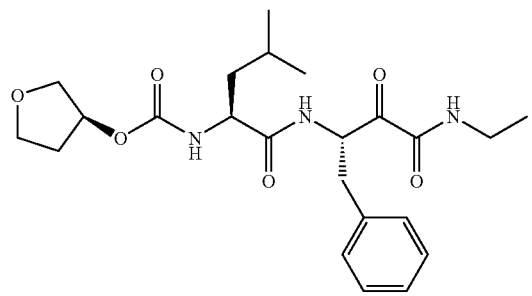

Following the reaction in an analogous manner to Example 1 and using the compound of Reference Example 2 in place of the compound of Reference Example 1, there was obtained the title compound as colorless crystals, via ((1S)-1-((((1S)-1-benzyl-3-ethylamiino-2-hydroxy-3-oxopropyl)amino)carbonyl)-3-methylbutyl)carbamic acid (3S)-tetrahydrofuran-3-yl ester.

M.p. 158.9-160.7° C.

$^1$H-NMR (300 MHz, DMSO-$d_6$) δ 0.83 (d, 3H, J=6.6), 0.85 (d, 3H, J=6.9), 1.04 (t, 3H, J=7.1), 1.35 (m, 2H), 1.55 (m, 1H), 1.83 (m, 1H), 2.08 (m, 1H), 2.82 (m, 1H), 3.14 (m, 3H), 3.61-3.78 (m, 4H), 4.01 (m, 1H), 5.07 (m, 1H), 5.19 (m, 1H), 7.17-7.33 (m, 6H), 8.22 (d, 1H, J=7.2), 8.69 (t, 1H, J=5.7).

MALDI-TOF-MS:$C_{23}H_{33}N_3O_6$(M+H)$^+$, 448.2447, Found: 448.2509.

Example 3

((1S)-1-((((1S)-1-Benzyl-2,3-dioxo-3-(ethylamino) propyl)amino)carbonyl)-3-methylbutyl)carbamic acid tetrahydro-4H-pyran-4-yl ester (Compound 3)

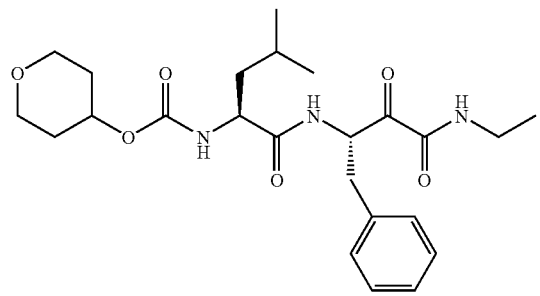

Following the reaction in an analogous manner to Example 1 and using the compound of Reference Example 3 in place of the compound of Reference Example 1, there was obtained the title compound as colorless crystals, via ((1S)-1-((((1S)-1-benzyl-3-ethylamino-2-hydroxy-3-oxopropyl)amino)carbonyl)-3-methylbutyl)carbamic acid tetrahydro-4H-pyran-4-yl ester.

M.p. 140.0-141.8° C.

$^1$H-NMR (300 MHz, DMSO-$d_6$) δ0.84 (m, 6H), 1.04 (t, 3H, J=7.2), 1.35 (m, 2H), 1.49 (m, 3H), 1.79 (m, 2H), 2.82 (m,

1H), 3.14 (m, 3H), 3.41 (m, 2H), 3.78 (m, 2H), 4.02 (m, 1H), 4.66 (m, 1H), 5.19 (m, 1H), 7.15-7.33 (m, 6H), 8.22 (d, 1H, J=7.2), 8.69 (t, 1H, J=5.7).
MALDI-TOF-MS:$C_{24}H_{35}N_3O_6$(M+Na)$^+$, 484.2424, Found: 484.2486.

Example 4

((1S)-1-((((1S)-1-Benzyl-2,3-dioxo-3-(cyclopropylamino)propyl)amino)carbonyl)-3-methylbutyl)carbamic acid 2-methoxyethyl ester (Compound 4)

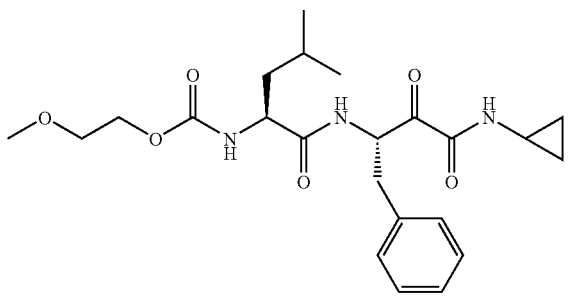

Following the reaction in an analogous manner to Example 1 and using the compound of Reference Example 9 in place of the compound of Reference Example 8, there was obtained the title compound as colorless crystals, via ((1S)-1-((((1S)-1-benzyl-3-cyclopropylamino-2-hydroxy-3-oxo-propyl)amino)carbonyl)-3-methylbutyl)carbamic acid 2-methoxyethyl ester.
M.p. 112.4-113.5° C.
$^1$H-NMR (300 MHz, DMSO-$d_6$) δ 0.58 (m, 2H), 0.65 (m, 2H), 0.83 (d, 3H, J=6.6), 0.85 (d, 3H, J=6.6), 1.35 (m, 2H), 1.56 (m, 1H), 2.68-2.88 (m, 2H), 3.11 (m, 1H), 3.25 (s, 3H), 3.47 (t, 2H, J=4.5), 4.04 (m, 3H), 5.17 (m, 1H), 7.17-7.34 (m, 6H), 8.25 (d, 1H, J=7.2), 8.73 (d, 1H, J=4.8).
MALDI-TOF-MS:$C_{23}H_{33}N_3O_6$(M+Na)$^+$, 470.2267, Found: 470.2441.
$[α]_D^{25}$+6.3° (c0.20,DMSO)

Example 5

((1S)-1-((((1S)-1-Benzyl-3-(cyclopropylamino)-2,3-dioxo-propyl)amino)carbonyl)-3-methylbutyl)carbamic acid (3S)-tetrahydrofuran-3-yl ester (Compound 5)

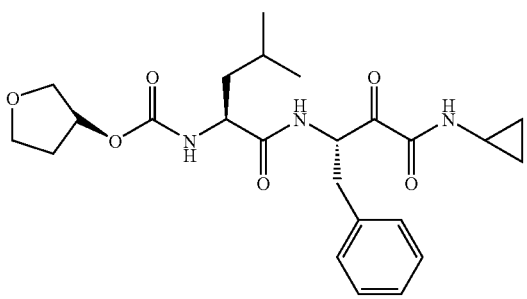

Following the reaction in an analogous manner to Example 1 and using the compound of Reference Example 2 in place of the compound of Reference Example 1, and the compound of Reference Example 9 in place of the compound of Reference Example 8, there was obtained the title compound as colorless crystals, via ((1S)-1-((((1S)-benzyl-3-cyclopropylamino-2-hydroxy-3-oxopropyl)amino)carbonyl)-3-methylbutyl)carbamic acid (3S)-tetrahydrofuran-3-yl ester.
M.p. 169.2-170.5° C.

$^1$H-NMR (300 MHz, DMSO-$d_6$) δ 0.58 (m, 2H), 0.65 (m, 2H), 0.83 (d, 3H, J=8.1), 0.85 (d, 3H, J=6.9), 1.34 (m, 2H), 1.55 (m, 1H), 1.83 (m, 1H), 2.08 (m, 1H), 2.79 (m, 2H), 3.12 (m, 1H), 3.61-3.80 (m, 4H), 4.02 (m, 1H), 5.08 (m, 1H), 5.17 (m, 1H), 7.22-7.35 (m, 6H), 8.24 (d, 1H, J=6.6), 8.74 (d, 1H, J=5.1).

MALDI-TOF-MS:$C_{24}H_{33}N_3O_6$(M+Na)$^+$, 482.2267, Found: 482.2586.

Example 6

((1S)-1-((((1S)-1-Benzyl-3-cyclopropylamino-2,3-dioxo-propyl)amino)carbonyl)-3-methylbutyl)carbamic acid tetrahydro-4H-pyran-4-yl ester (Compound 6)

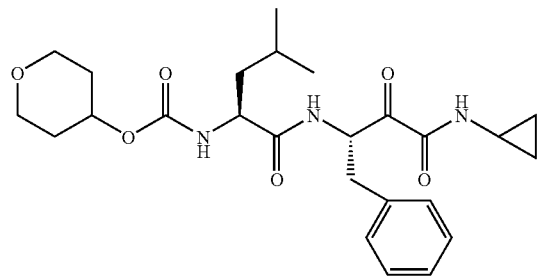

Following the reaction in an analogous manner to Example 1 and using the compound of Reference Example 3 in place of the compound of Reference Example 1, and the compound of Reference Example 9 in place of the compound of Reference Example 8, there was obtained the title compound as colorless crystals, via ((1S)-1-((((1S)-1-benzyl-3-cyclopropylamino-2-hydroxy-3-oxopropyl)amino)carbonyl)-3-methylbutyl)carbamic acid tetrahydro-4H-pyran-4-yl ester.
M.p. 137.0-138.2° C.
$^1$H-NMR (300 MHz, DMSO-$d_6$) δ 0.58 (m, 2H), 0.65 (m, 2H), 0.84 (m, 6H), 1.35 (m 2H), 1.48 (m, 3H), 1.80 (m, 2H), 2.79 (m, 2H), 3.11 (m, 1H), 3.41 (m, 2H), 3.79 (m, 2H), 4.03 (m, 1H), 4.65 (m, 1H), 5.18 (m, 1H), 7.15-7.30 (m, 6H), 8.23 (d, 1H, J=6.9), 8.73 (d, 1H, J=5.4).
MALDI-TOF-MS:$C_{25}H_{35}N_3O_6$(M+H)$^+$, 474.2604, Found: 474.2643.

Example 7

((1S)-1-(((((1S)-1-Benzyl-2,3-dioxo-3-(propylamino)propyl)amino)carbonyl)-3-methylbutyl)carbamic acid 2-methoxyethyl ester (Compound 7)

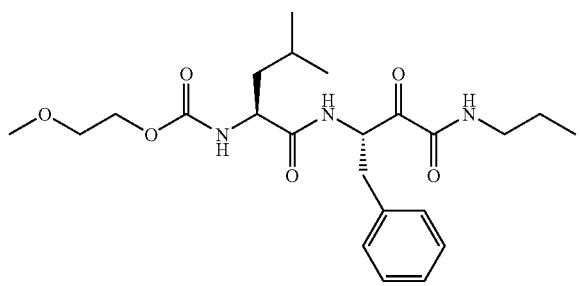

Following the reaction in an analogous manner to Example 1 and using the compound of Reference Example 10 in place of the compound of Reference Example 8, there was obtained the title compound as colorless crystals, via ((1S)-1-((((1S)-1-benzyl-2-hydroxy-3-oxo-3-(propylamino)propyl)amino)carbonyl)-3-methylbutyl)carbamic acid 2-methoxyethyl ester.

M.p. 108.8-109.9° C.

$^1$H-NMR (30 MHz, DMSO-$d_6$) δ 0.83 (m, 9H), 1.35 (m, 2H), 1.46 (m, 2H), 1.55 (m, 1H), 2.83 (dd, 1H, J=14.0, 9.2), 3.08 (m, 3H), 3.25 (s, 3H), 3.48 (t, 2H, J=4.4), 4.04 (m, 3H), 5.19 (m, 1H), 7.22-7.28 (m, 6H), 8.24 (d, 1H, J=6.9), 8.68 (t, 1H, J=5.6).

MALDI-TOF-MS:$C_{23}H_{35}N_3O_6$(M+H)$^+$, 450.2604, Found: 450.2832.

Example 8

((1S)-1-(((((1S)-1-Benzyl-2,3-dioxo-3-(cyclobutylamino)propyl)amino)carbonyl)-3-methylbutyl)carbamic acid 2-methoxyethyl ester (Compound 8)

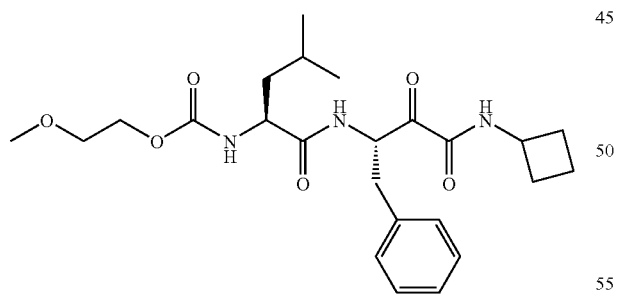

Following the reaction in an analogous manner to Example 1 and using the compound of Reference Example 11 in place of the compound of Reference Example 8, there was obtained the title compound as colorless crystals, via ((1S)-1-((((1S)-1-benzyl-3-cyclobutylamino-2-hydroxy-3-oxopropyl)amino)carbonyl)-3-methylbutyl)carbamic acid 2-methoxyethyl ester.

M.p. 114.2-115.3° C.

$^1$H-NMR (300 MHz, DMSO-$d_6$) δ 0.84 (m, 6H), 1.34 (m, 2H), 1.49-1.72 (m, 3H), 2.10 (m, 4H), 2.81 (dd, 1H, J=13.8, 9.3), 3.10 (m, 1H), 3.25 (s, 3H), 3.47 (m, 2H), 4.03 (m, 3H), 4.22 (m, 1H), 5.15 (m, 1H), 7.24 (m, 6H), 8.24 (d, 1H, J=7.2), 8.91 (d, 1H, J=7.8).

MALDI-TOF-MS:$C_{24}H_{35}N_3O_6$(M+Na)$^+$, 484.2424, Found: 484.2400.

Example 9

((1S)-1-((((1S)-1-Benzyl-3-butylamino-2,3-dioxopropyl)amino)carbonyl)-3-methylbutyl)carbamic acid 2-methoxyethyl ester (Compound 9)

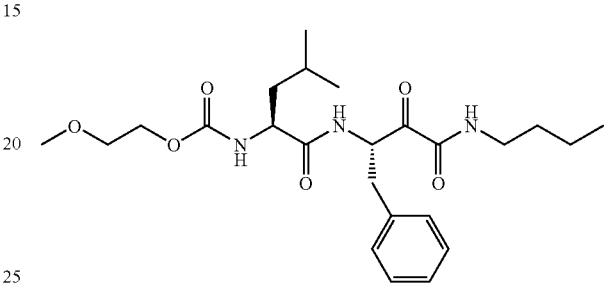

Following the reaction in an analogous manner to Example 1 and using the compound of Reference Example 12 in place of the compound of Reference Example 8, there was obtained the title compound as colorless crystals, via ((1S)-1-((((1S)-1-benzyl-3-butylamino-2-hydroxy-3-oxopropyl)amino)carbonyl)-3-methylbutyl)carbamic acid 2-methoxyethyl ester.

M.p. 94.0-95.2° C.

$^1$H-NMR (300 MHz, DMSO-$d_6$) δ 0.85 (m, 9H), 1.25 (m, 2H), 1.35 (m, 2H), 1.42 (m, 2H), 1.56 (m, 1H), 2.83 (dd, 1H, J=13.8, 9.0), 3.10 (m, 3H), 3.25 (s, 3H), 3.47 (t, 2H, J=4.5), 4.04 (m, 3H), 5.18 (m, 1H), 7.21-7.29 (m, 6H), 8.23 (d, 1H, J=6.6), 8.67 (t, 1H, J=6.0).

MALDI-TOF-MS:$C_{24}H_{37}N_3O_6$(M+H)$^+$, 464.2760, Found: 464.2870.

Example 10

((1S)-1-((((1S)-1-Benzyl-2,3-dioxo-3-(2,2,2-trifluoroethylamino)propyl)amino)carbonyl)-3-methylbutyl)carbamic acid 2-methoxyethyl ester (Compound 10)

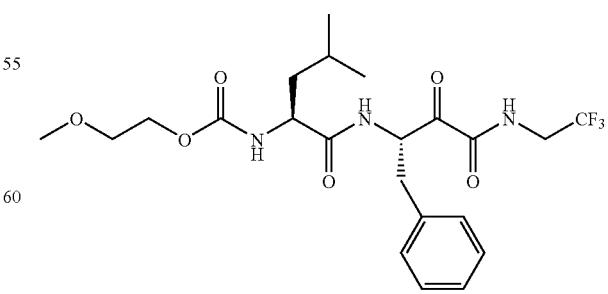

Following the reaction in an analogous manner to Example 1 and using the compound of Reference Example 13 in place of the compound of Reference Example 8, there was obtained the title compound as colorless crystals, via ((1S)-1-((((1S)-1-benzyl-2-hydroxy-3-oxo-3-(2,2,2-trifluoroethyl-amino)propyl)amino)carbonyl)-3-methylbutyl)carbamic acid 2-methoxyethyl ester.

M.p. 152.5-153.9° C.

$^1$H-NMR (300 MHz, DMSO-$d_6$) δ 0.84 (m, 6H), 1.34 (m, 2H), 1.55 (m, 1H), 2.86 (dd, 1H, J=14.0, 8.6), 3.10 (dd, 1H, J=14.1, 4.8), 3.25 (s, 3H), 3.48 (t, 2H, J=4.7), 3.90 (m, 2H), 4.04 (m, 3H), 5.14 (m, 1H), 7.21-7.31 (m, 6H), 8.34 (d, 1H, J=6.9), 9.29 (m, 1H).

MALDI-TOF-MS:$C_{22}H_{30}F_3N_3O_6$(M+H)$^+$, 490.2165, Found: 490.2434.

Example 11

(((1S)-1-((((1S)-1-Benzyl-2,3-dioxo-3-(2-indanylamino)propyl)amino)carbonyl)-3-methylbutyl)carbamic acid 2-methoxyethyl ester (Compound 11)

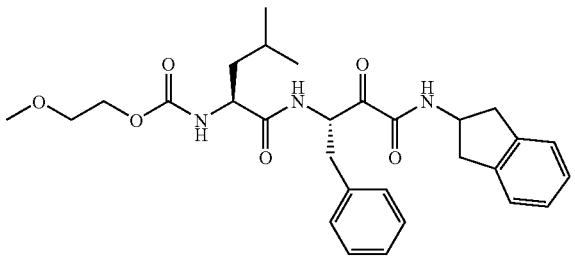

Following the reaction in an analogous manner to Example 1 and using the compound of Reference Example 14 in place of the compound of Reference Example 8, there was obtained the title compound as colorless crystals, via ((1S)-1-((((1S)-1-benzyl-2-hydroxy-3-(2-indanylamino)-3-oxopropyl)amino)carbonyl)-3-methylbutyl)carbamic acid 2-methoxyethyl ester.

M.p. 141.9-143.5° C.

$^1$H-NMR (300 MHz, DMSO-$d_6$) δ 0.83 (d, 3H, J=6.9), 0.86 (d, 3H, J=6.9), 1.36 (m, 2H), 1.57 (m, 1H), 2.80-2.96 (m, 3H), 3.10-3.18 (m, 3H), 3.24 (s, 3H), 3.47 (t, 2H, J=4.7), 4.04 (m, 3H), 4.50 (m, 1H), 5.19 (m, 1H), 7.13-7.30 (m, 10H), 8.29 (d, 1H, J=6.9), 8.97 (d, 1H, J=7.2).

MALDI-TOF-MS:$C_{29}H_{37}N_3O_6$(M+H)$^+$, 524.2760, Found: 524.2810.0

Example 12

((1S)-1-((((1S)-1-Benzyl-2,3-dioxo-3-(2-methoxyethylamino)propyl)amino)carbonyl)-3-methylbutyl)carbamic acid 2-methoxyethyl ester (Compound 12)

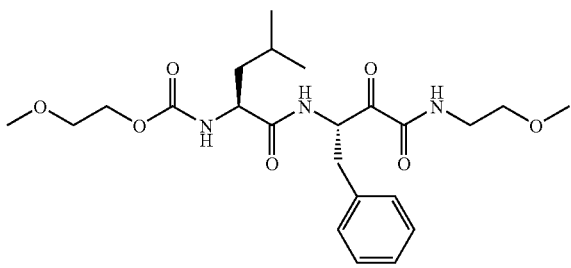

Following the reaction in an analogous manner to Example 1 and using the compound of Reference Example 15 in place of the compound of Reference Example 8, the title compound was obtained as colorless crystals, via ((1S)-1-((((1S)-1-benzyl-2-hydroxy-3-(2-methoxyethylamino)-3-oxopropyl)amino)carbonyl)-3-methylbutyl)carbamic acid 2-methoxyethyl ester M.p. 127.0-127.9° C.

$^1$H-NMR (300 MHz, DMSO-$d_6$) δ 0.83 (d, 3H, J=6.9), 0.86 (d, 3, J=6.9), 1.35 (m, 2H), 1.56 (m, 1H), 2.83 (dd, 1H, J=13.8, 9.0), 3.11 (dd, 1H, J=14.0, 4.4), 3.24 (s, 3H), 3.25 (s, 3H), 3.16-3.34 (m, 2H), 3.39 (m, 2H), 3.48 (t, 2H, J=4.5), 4.04 (m, 3H), 5.20 (m, 1H), 7.18-7.30 (m, 6H), 8.21 (d, 1H, J=6.9), 8.66 (t, 1H, J=5.4).

MALDI-TOF-MS:$C_{23}H_{35}N_3O_7$(M+Na)$^+$, 488.2373, Found: 488.2680.

Example 13

((1S)-1-((((1S)-2,3-Dioxo-3-ethylamino-1-(phenylethyl)propyl)amino)carbonyl)-3-methylbutyl)carbamic acid 2-methoxyethyl ester (Compound 13)

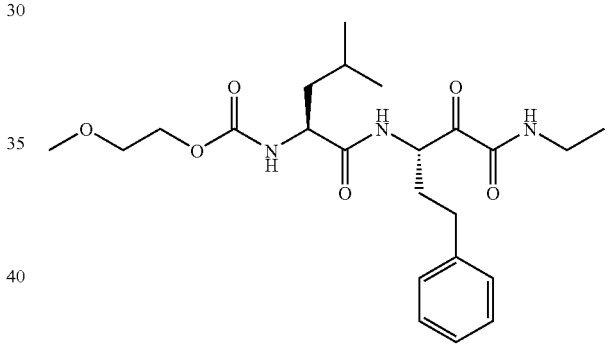

Following the reaction in an analogous manner to Example 1 and using the compound of Reference Example 16 in place of the compound of Reference Example 8, the title compound was obtained as colorless crystals, via ((1S)-1-((((1S)-3-ethylamino-2-hydroxy-3-oxo-1-(phenylethyl)propyl)amino)carbonyl)-3-methylbutyl)carbamic acid 2-methoxyethyl ester.

M.p. 119.1-120.4° C.

$^1$H-NMR (300 MHz, DMSO-$d_6$) δ 0.89 (t, 6H, J=6.3), 1.03 (t, 3H, J=7.2), 1.43 (t, 2H, J=7.2), 1.61-1.85 (m, 2H), 2.07 (m, 1H), 2.56-2.74 (m, 2H), 3.07-3.17 (m, 2H), 3.25 (s, 3H), 3.49 (t, 2H, J=4.7), 4.05-4.14 (m, 3H), 4.89 (m, 1H), 7.16-7.36 (m, 5H), 7.34 (d, 1H, J=8.4), 8.33 (d, 1H, J=6.9), 8.65 (t, 1H, J=5.9).

MALDI-TOF-MS:$C_{23}H_{35}N_3O_6$(M+H)$^+$, 450.2604, Found: 450.2701.

Example 14

((1S)-1-(((((1S)-2,3-Dioxo-3-ethylamino-1-(phenylethyl)propyl)amino)carbonyl)-3-methylbutyl)carbamic acid (3S)-tetrahydrofuran-3-yl ester (Compound 14)

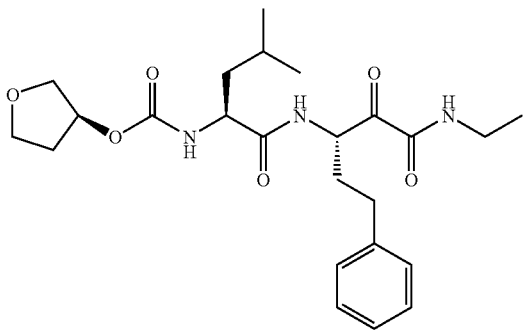

Following the reaction in an analogous manner to Example 1 and using the compounds of Reference Examples 2 and 16 in place of the compounds of Reference Examples 1 and 8 respectively, the title compound was obtained as colorless crystals, via ((1S)-1-(((((1S)-3-ethylamino-2-hydroxy-3-oxo-1-(phenylethyl)propyl)amino)carbonyl)-3-methylbutyl)carbamic acid (3S)-tetrahydrofuran-3-yl ester.

M.p. 111.9-114.5° C.

$^1$H-NMR (300 MHz, DMSO-$d_6$) δ 0.89 (t, 6H, J=6.3), 1.03 (t, 3H, J=7.2), 1.43 (t, 2H, J=7.4), 1.60-1.91 (m, 3H), 2.09 (m, 2H), 2.56-2.76 (m, 2H), 3.07-3.17 (m, 2H), 3.63-3.82 (m, 4H), 4.02-4.13 (m, 1H), 4.88 (m, 1H), 5.09-5.13 (m, 1H), 7.16-7.31 (m, 5H), 7.34 (d, 1H, J=8.4), 8.34 (d, 1H, J=6.9), 8.66 (t, 1H, J=5.7).

MALDI-TOF-MS:$C_{24}H_{35}N_3O_6(M+H)^+$, 462.2604, Found: 462.2870.

Example 15

((1S)-1-(((((1S)-2,3-Dioxo-3-cyclopropylamino-1-(phenylethyl)propyl)amino)carbonyl)-3-methylbutyl) carbamic acid 2-methoxyethyl ester (Compound 15)

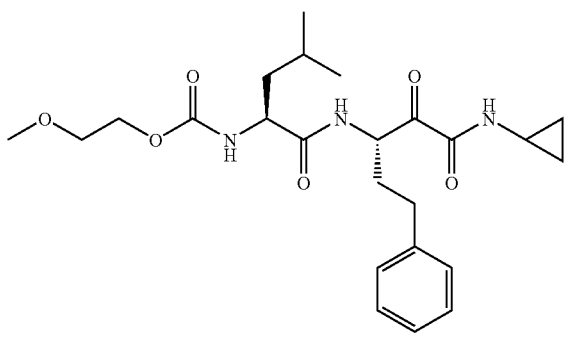

Following the reaction in an analogous manner to Example 1 and using the compound of Reference Example 17 in place of the compound of Reference Example 8, the title compound was obtained as colorless crystals, via ((1S)-1-(((((1S)-3-cyclopropylamino-2-hydroxy-3-oxo-1-(phenylethyl)propyl)amino)carbonyl)-3-methylbutyl)carbamic acid 2-methoxyethyl ester.

M.p. 109.7-111.1° C.

$^1$H-NMR (300 MHz, DMSO-$d_6$) δ 0.53-0.68 (m, 4H), 0.87-0.91 (m, 6H), 1.43 (t, 3H, J=7.2), 1.59-1.85 (m, 2H), 2.01-2.13 (m, 1H), 2.56-2.74 (m, 3H), 3.25 (s, 3H), 3.48-3.51 (m, 2H), 4.05-4.14 (m, 3H), 4.87 (m, 1H), 7.17-7.36 (m, 6H), 8.34 (d, 1H, J=6.6), 8.69 (d, 1H, J=5.1).

MALDI-TOF-MS:$C_{24}H_{35}N_3O_6(M+H)^+$, 462.2604, Found: 462.2742.

Example 16

((1S)-1-(((((1S)-2,3-Dioxo-3-cyclopropylamino-1-(phenylethyl)propyl)amino)carbonyl)-3-methylbutyl) carbamic acid (3S)-tetrahydro-furan-3-yl ester (Compound 16)

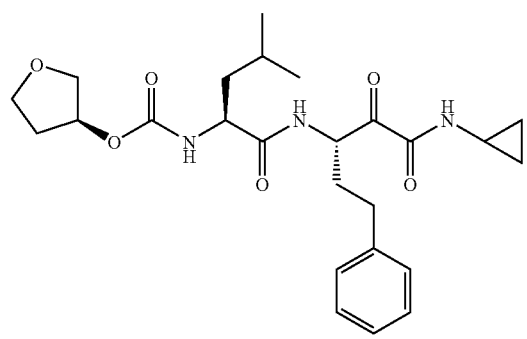

Following the reaction in an analogous manner to Example 1 and using the compounds of Reference Examples 2 and 17 in place of the compounds of Reference Examples 1 and 8 respectively, the title compound was obtained as colorless crystals, via ((1S)-1-(((((1S)-3-cyclopropylamino-2-hydroxy-3-oxo-1-(phenylethyl)propyl)amino)carbonyl)-3-methylbutyl)carbamic acid (3S)-tetrahydrofuran-3-yl ester.

M.p. 115.8-116.2° C.

$^1$H-NMR (300 MHz, DMSO-$d_6$) δ 0.56-0.59 (m, 4H), 0.88 (t, 6H, J=6.3), 1.42 (t, 2H, J=7.4), 1.60-1.91 (m, 3H), 2.09(m, 2H), 2.56-2.76 (m, 3H), 3.63-3.81 (m, 4H), 4.05-4.13 (m, 1H), 4.87 (m, 1H), 5.09-5.13 (m, 1H), 7.20-7.35 (m, 6H), 8.34 (d, 1H, J=6.9), 8.69 (d, 1H, J=5.1).

MALDI-TOF-MS:$C_{29}H_{35}N_3O_6(M+H)^+$, 474.2604, Found: 474.2598.

Example 17

((1S)-1-(((((1S)-1-Benzyl-2,3-dioxo-3-(cyclopropylamino)propyl)amino)carbonyl)-3-methylbutyl)carbamic acid 5-methoxy-3-oxapentyl ester (Compound 17)

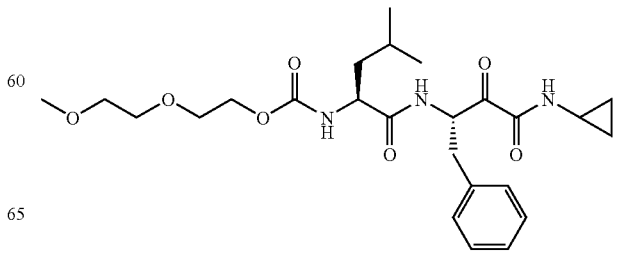

Following the reaction in an analogous manner to Example 1 and using the compounds of Reference Examples 4 and 9 in place of the compounds of Reference Examples 1 and 8 respectively, the title compound was obtained as colorless crystals, via ((1S)-1-((((1S)-1-benzyl-3-cyclopropylamino-2-hydroxy-3-oxopropyl)amino)carbonyl)-3-methylbutyl) carbamic acid 5-methoxy-3-oxapentyl ester.

M.p. 127.9-128.7° C.

$^1$H-NMR (300 MHz, DMSO-$d_6$) δ 0.54-0.66 (m, 4H), 0.81-0.86 (m, 6H), 1.30-1.42 (m, 2H), 1.57 (m, 1H), 2.73 (m, 1H), 2.82 (dd, 1H, J=14.3, 9.2), 3.11 (dd, 1H, J=13.8, 4.2), 3.24 (s, 3H), 3.42-3.44 (m, 2H), 3.50-3.57 (m, 4H), 3.99-4.04 (m, 3H), 5.17 (m, 1H), 7.22-7.30 (m, 6H), 8.22 (d, 1H, J=6.9), 8.71 (d, 1H, J=4.8).

MALDI-TOF-MS:$C_{25}H_{37}N_3O_7$(M+Na)$^+$, 514.2530, Found: 514.2944.

$[α]_D^{25}$+13.9°(c 0.20,DMSO)

Example 18

((1S)-1-((((1S)-1-Benzyl-2,3-dioxo-3-(cyclopropylamino)propyl)amino)carbonyl)-3-methylbutyl)carbamic acid 8-methoxy-3,6-dioxaoctyl ester (Compound 18)

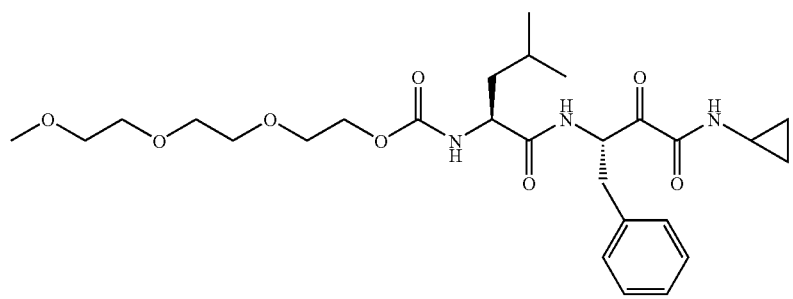

Following the reaction in an analogous manner to Example 1 and using the compounds of Reference Examples 5 and 9 in place of the compounds of Reference Examples 1 and 8 respectively, the title compound was obtained as colorless crystals, via ((1S)-1-((((1S)-1-benzyl-3-cyclopropylamino-2-hydroxy-3-oxopropyl)amino)carbonyl)-3-methylbutyl) carbamic acid 8-methoxy-3,6-dioxaoctyl ester.

M.p. 116.0-117.2° C.

$^1$H-NMR (300 MHz, DMSO-$d_6$) δ 0.58 (m, 2H), 0.65 (m, 2H), 0.83 (d, 3H, J=7.8), 0.85 (d, 3H, J=6.9), 1.35 (m, 2H), 1.57 (m, 1H), 2.73-2.86 (m, 2H), 3.11 (m, 1H), 3.24 (s, 3H), 3.44 (m, 2H), 3.51 (m, 6H), 3.56 (t, 2H, J=4.7), 4.04 (m, 3H), 5.17 (m, 1H), 7.22-7.31 (m, 6H), 8.25 (d, 1H, J=6.9), 8.73 (d, 1H, J=5.1).

MALDI-TOF-MS:$C_{27}H_{41}N_3O_8$(M+Na)$^+$, 558.2792, Found: 558.2717.

$[α]_D^{25}$+2.5° (c 0.20,DMSO)

Example 19

((1S)-1-((((1S)-1-Benzyl-2,3-dioxo-3-(cyclopropylamino)propyl)amino)carbonyl)-3-methylbutyl)carbamic acid 11-methoxy-3,6,9-trioxaundecanyl ester (Compound 19)

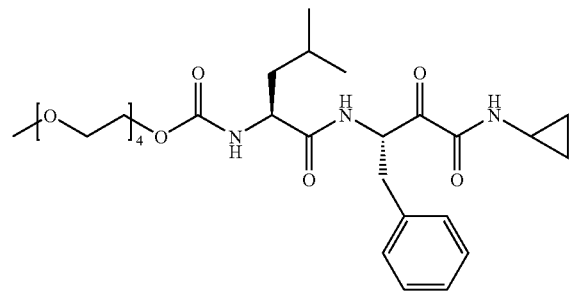

Following the reaction in an analogous manner to Example 1 and using the compounds of Reference Examples 6 and 9 in place of the compounds of Reference Examples 1 and 8 respectively, the title compound was obtained as colorless crystals, via ((1S)-1-((((1S)-1-benzyl-3-cyclopropylamino-2-hydroxy-3-oxopropyl)amino)carbonyl)-3-methylbutyl) carbamic acid 11-methoxy-3,6,9-trioxaundecanyl ester.

M.p. 97.5-98.5° C.

$^1$H-NMR (300 MHz, DMSO-$d_6$) δ 0.54-0.66 (m, 4H), 0.81-0.86 (m, 6H), 1.32-1.37 (m, 2H), 1.56 (m, 1H), 2.73 (m, 1H), 2.82 (dd, 1H, J=14.0, 9.2), 3.11 (dd, 1H, J=14.1, 4.2), 3.24 (s, 3H), 3.41-3.44 (m, 2H), 3.50-3.51 (m, 10H), 3.54-3.57 (m, 2H), 3.99-4.08 (m, 3H), 5.16 (m, 1H), 7.22-7.31 (m, 6H), 8.25 (d, 1H, J=7.2), 8.73 (d, 1H, J=5.1).

MALDI-TOF-MS:$C_{29}H_{45}N_3O_9$(M+Na)$^+$, 602.3054, Found: 602.3427.

$[α]_D^{25}$+6.9° (c 0.20,DMSO)

Example 20
((1S)-1-((((1S)-1-Benzyl-2,3-dioxo-3-(cyclopropylamino)propyl)amino)carbonyl)-3-methylbutyl)carbamic acid 14-methoxy-3,6,9,12-tetraoxa-tetradecanyl ester (Compound 20)

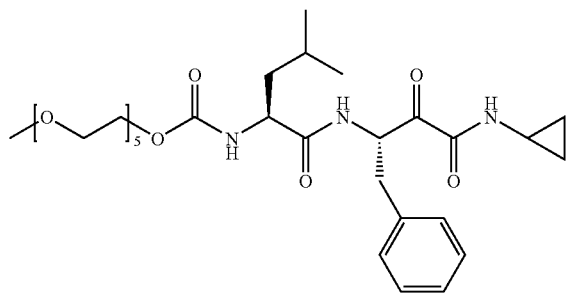

Following the reaction in an analogous manner to Example 1 and using the compounds of Reference Examples 7 and 9 in place of the compounds of Reference Examples 1 and 7 respectively, the title compound was obtained as colorless crystals, via ((1S)-1-(((((1S)-1-benzyl-3-cyclopropylamino-2-hydroxy-3-oxopropyl)amino)carbonyl)-3-methylbutyl) carbamic acid 14-methoxy-3,6,9,12-tetraoxatetradecanyl ester.

M.p. 98.5-99.9° C.

$^1$H-NMR (300 MHz, DMSO-d$_6$) δ 0.58 (m, 2H), 0.65 (m, 2H), 0.83 (d, 3H, J=6.9), 0.85 (d, 3H, J=7.8), 1.35 (m, 2H), 1.57 (m, 1H), 2.73-2.86 (m, 2H), 3.11 (m, 1H), 3.24 (s, 3H), 3.42 (m, 2H), 3.51 (m, 14H), 3.56 (t, 2H, J=3.3), 4.04 (m, 3H), 5.17 (m, 1H), 7.22-7.30 (m, 6H), 8.24 (d, 1H, J=6.9), 8.72 (d, 1H, J=4.5).

MALDI-TOF-MS:C$_{31}$H$_{49}$N$_3$O$_{10}$(M+Na)$^+$, 646.3316, Found: 646.3404.

Example 21
((1S)-1-((((1S)-2,3-Dioxo-1-(2-methylpropyl)-3-(2-phenoxyethyl)aminopropyl)amino)carbonyl)-3-methylbutyl)carbamic acid 2-methoxyethyl ester (Compound 21)

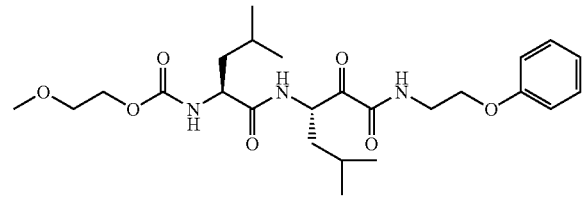

Following the reaction in an analogous manner to Example 1 and using the compound of Reference Examples 18 in place of the compound of Reference Example 8, the title compound was obtained as colorless crystals, via ((1S)-1-((((1S)-2-hydroxy-1-(2-methylpropyl)-3-oxo-3-(2-phenoxyethyl)aminopropyl)amino)carbonyl)-3-methylbutyl)carbamic acid 2-methoxyethyl ester.

M.p. 99.7-100.5° C.

$^1$H-NMR (300 MHz, DMSO-d$_6$) δ 0.88 (dd, 12H, J=12.0, 6.3), 1.35-1.54 (m, 4H), 1.58-1.75 (m, 2H), 3.25 (s, 3H), 3.46-3.53 (m, 4H), 4.03-4.07 (m, 5H), 5.06 (m, 1H), 6.91-6.95 (m, 3H), 7.26-7.31 (m, 3H), 8.15 (d, 1H, J=7.2), 8.81(t, 1H, J=5.9).

MALDI-TOF-MS:C$_{25}$H$_{39}$N$_3$O$_7$(M+H)$^+$, 494.2866, Found: 494.2967.

Example 22
((1S)-1-((((1S)-2,3-Dioxo-1-(2-methylpropyl)-3-(2-phenoxyethyl)aminopropyl)amino)carbonyl)-3-methylbutyl)carbamic acid 5-methoxy-3-oxapentyl ester (Compound 22)

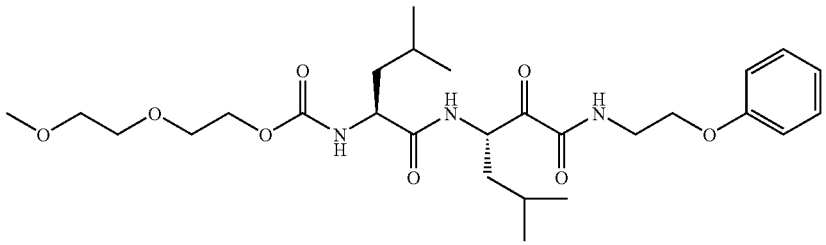

Following the reaction in an analogous manner to Example 1 and using the compounds of Reference Examples 4 and 18 in place of the compounds of Reference Examples 1 and 8 respectively, the title compound was obtained as colorless crystals, via ((1S)-1-((((1S)-2-hydroxy-1-(2-methylpropyl)-3-oxo-3-(2-phenoxyethyl)aminopropyl)amino)carbonyl)-3-methylbutyl)carbamic acid 5-methoxy-3-oxapentyl ester.

M.p. 53.5-54.1° C.

$^1$H-NMR (300 MHz, DMSO-d$_6$) δ 0.87 (dd, 12H, J=12.2, 6.5), 1.35-1.54 (m, 4H), 1.58-1.75 (m, 2H), 3.24 (s, 3H), 3.41-3.45 (m, 2H), 3.47-3.57 (m, 6H), 4.03-4.07 (m, 5H), 5.06 (m, 1H), 6.91-6.96 (m, 3H), 7.26-7.31 (m, 3H), 8.17 (d, 1H, J=6.9), 8.83 (t, 1H, J=5.7).

MALDI-TOF-MS:C$_{27}$H$_{43}$N$_3$O$_8$(M+H)$^+$, 538.3128, Found: 538.3140.

Example 23

(((1S)-1-(((((1RS)-3-amino-1-benzyl-2,3-dioxopropyl)amino)carbonyl)-3-methylbutyl)carbamic acid 5-methoxy-3-oxapentyl ester (Compound 23)

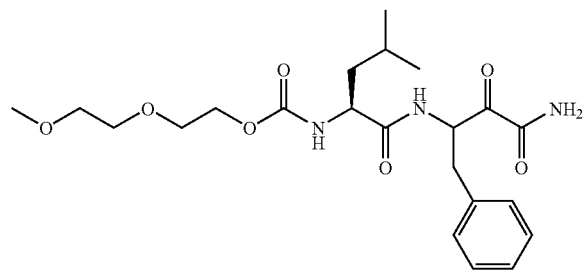

Following the reaction in an analogous manner to Example 1 and using the compounds of Reference Examples 4 and 19 in place of the compounds of Reference Examples 1 and 8 respectively, the title compound was obtained as colorless crystals, via ((1S)-1-(((((1RS)-3-amino-1-benzyl-2-hydroxy-3-oxo -propyl)amino)carbonyl)-3-methylbutyl)carbamic acid 5-methoxy-3-oxapentyl ester.

$^1$H-NMR (300 MHz, DMSO-$d_6$) δ 0.77 (d, 3H, J=6.3), 0.83 (d, 1.5H, J=6.6), 0.86 (d, 1.5H, J=6.9), 1.05-1.63 (m, 3H), 2.68-2.85 (m, 1H), 3.12 (m, 1H), 3.23 (s, 3H), 3.42 (m, 2H), 3.51-3.56 (m, 4H), 4.03 (m, 3H), 5.22 (m, 1H), 7.21-7.31 (m, 6H), 7.81 (d, 1H, J=14), 8.06 (d, 1H, J=18), 8.19 (d, 0.5H, J=6.9), 8.26 (d, 0.5H, J=7.5).

Example 24

((1S)-1-(((((1S)-1-benzyl-3-(cyclopropylamino)-2,3-dioxo-propyl)amino)carbonyl)-3-methylbutyl)carbamic acid 2-(pyridin-2-yl)ethyl ester (Compound 24)

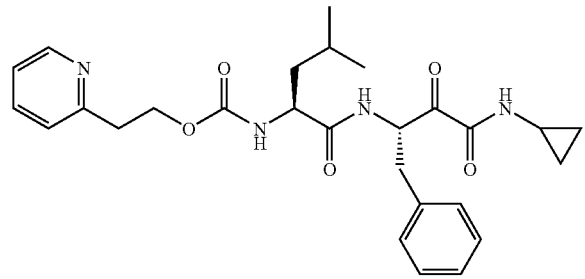

Following the reaction in an analogous manner to Example 1 and using the compounds of Reference Examples 20 and 9 in place of the compounds of Reference Examples 1 and 8 respectively, the title compound was obtained as colorless crystals, via ((1S)-1-(((((1S)-1-benzyl-3-(cyclopropylamino)-2-hydroxy-3-oxopropyl)amino)carbonyl)-3-methylbutyl)carbamic acid 2-(pyridin-2-yl)ethyl ester.

$^1$H-NMR (300 MHz, DMSO-$d_6$) δ 0.58-0.66 (m, 4H), 0.83 (t, 6H, J=7.1), 1.31-1.35 (m, 2H), 1.53 (m, 1H), 2.74 (m, 1H), 2.81 (dd, 1H, J=14.1, 9.3), 3.02 (t, 2H, J=6.3), 3.11 (dd, 1H, J=14.0, 4.1), 4.01 (m, 1H), 4.28-4.32 (m, 2H), 5.17 (m, 1H), 7.14-7.34 (m, 8H), 7.75 (t, 1H, J=6.8), 8.23 (d, 1H, J=7.2), 8.51 (d, 1H, J=4.2), 8.71 (d, 1H, J=4.5).

Example 25

((1S)-1-(((((1S)-1-Benzyl-3-(cyclopropylamino)-2,3-dioxopropyl)amino)carbonyl)-3-methylbutyl)carbamic acid 2-(6-methylpyridin-2-yl)ethyl ester (Compound 25)

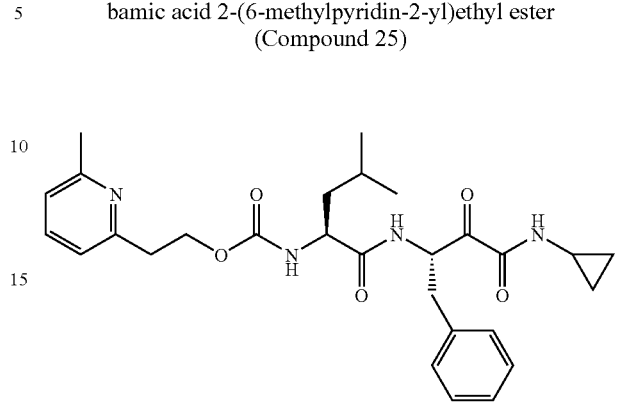

Following the reaction in an analogous manner to Example 1 and using the compounds of Reference Examples 21 and 9 in place of the compounds of Reference Examples 1 and 8 respectively, the title compound was obtained as colorless crystals, via (((1S)-1-(((((1S)-1-benzyl-3-(cyclopropylamino)-2-hydroxy-3-oxopropyl)amino)carbonyl)-3-methylbutyl)carbamic acid 2-(6-methylpyridin-2-yl)ethyl ester.

M.p. 162.0-163.6° C.

$^1$H-NMR (300 MHz, DMSO-$d_6$) δ 0.54-0.66 (m, 4H), 0.76-0.86 (m, 6H), 1.54 (m, 1H), 2.43 (s, 3H), 2.73-2.86 (m, 2H), 2.96 (t, 2H, J=6.5), 3.11 (m, 1H), 4.03 (m, 1H), 4.21-4.34 (m, 2H), 5.17 (m, 1H), 7.07-7.30 (m, 8H), 7.58 (t, 1H, J=7.7), 8.23 (d, 1H, J=6.9), 8.72 (d, 1H, J=4.8).

Example 26

((1S)-1-(((((1S)-1-Benzyl-3-(cyclopropylamino)-2,3-dioxopropyl)amino)carbonyl)-3-methylbutyl)carbamic acid 2-(5-ethylpyridin-2-yl)ethyl ester (Compound 26)

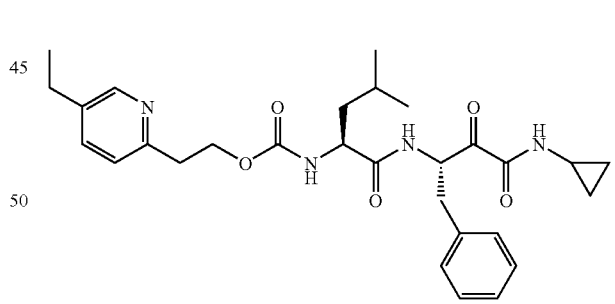

Following the reaction in an analogous manner to Example 1 and using the compounds of Reference Examples 22 and 9 in place of the compounds of Reference Examples 1 and 8 respectively, the title compound was obtained as colorless crystals, via ((1S)-1-(((((1S)-1-benzyl-3-(cyclopropylamino)-2-hydroxy-3-o xopropyl)amino)carbonyl)-3-methylbutyl)carbamic acid 2-(5-ethylpyridin-2-yl)ethyl ester.

M.p. 119.9-121.0° C.

$^1$H-NMR (300 MHz, DMSO-$d_6$) δ 0.58-0.66 (m, 4H), 0.75-0.85 (m, 6H), 1.17 (t, 3H, J=7.7), 1.33-1.36 (m, 2H), 1.53 (m, 1H), 2.58 (dd, 2H, J=15.5, 8.3), 2.74-2.85 (m, 2H), 2.94-2.98 (m, 2H), 3.12 (m, 1H), 4.04 (m, 1H), 4.28-4.29 (m,

2H), 5.17 (m, 1H), 7.13-7.26 (m, 7H), 7.55 (d, 1H, J=8.1), 8.22-8.35 (m, 2H), 8.75 (m, 1H).

Example 27

((1S)-1-((((1S)-1-Benzyl-3-(cyclopropylamino)-2,3-dioxopropyl)amino)carbonyl)-3-methylbutyl)carbamic acid 2-tert-butoxyethyl ester (Compound 27)

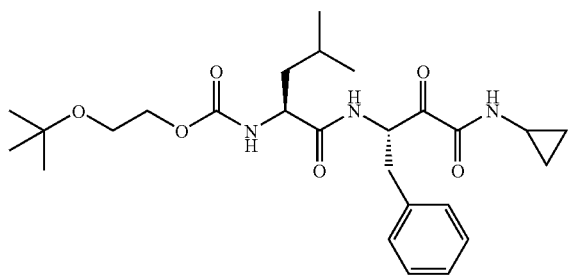

Following the reaction in an analogous manner to Example 1 and using the compounds of Reference Examples 23 and 9 in place of the compounds of Reference Examples 1 and 8 respectively, the title compound was obtained as colorless crystals, via ((1S)-1-((((1S)-1-benzyl-3-(cyclopropylamino)-2-hydroxy-3-oxopropyl)amino)carbonyl)-3-methylbutyl)carbamic acid 2-tert-butoxyethyl ester.

$^1$H-NMR (300 MHz, DMSO-$d_6$) δ 0.58 (m, 2H), 0.65 (m, 2H), 0.83 (d, 3H, J=7.5), 0.85 (d, 3H, J=6.9), 1.12 (s, 9H), 1.35 (m, 2H), 1.57 (m, 1H), 2.74 (m, 1H), 2.82 (m, 1H), 3.11 (m, 1H), 3.45 (m, 2H), 3.98 (m, 3H), 5.17 (m, 1H), 7.24 (m, 6H), 8.23 (d, 1H, J=6.6), 8.71 (d, 1H, J=4.8).

Example 28

((1S)-1-((((1S)-1-Benzyl-3-(cyclopropylamino)-2,3-dioxopropyl)amino)carbonyl)-3-methylbutyl)carbamic acid 2-isopropoxyethyloxyl ester (Compound 28)

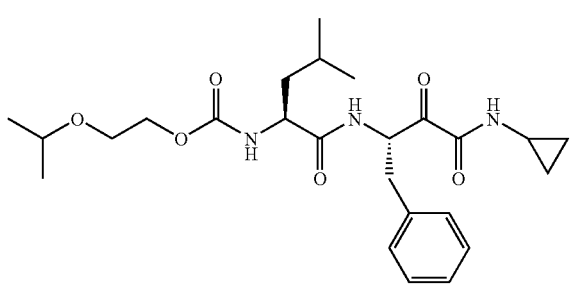

Following the reaction in an analogous manner to Example 1 and using the compounds of Reference Examples 24 and 9 in place of the compounds of Reference Examples 1 and 8 respectively, the title compound was obtained as colorless crystals, via ((1S)-1-((((1S)-1-benzyl-3-(cyclopropylamino)-2-hydroxy-3-oxopropyl)amino)carbonyl)-3-methylbutyl)carbamic acid 2-isopropoxyethyl ester.

$^1$H-NMR (300 MHz, DMSO-$d_6$) δ 0.58 (m, 2H), 0.65 (m, 2H), 0.83 (d, 3H, J=7.2), 0.85 (d, 3H, J=6.9), 1.07 (d, 6H, J=5.7), 1.35 (m, 2H), 1.57 (m, 1H), 2.74 (m, 1H), 2.82 (m, 1H), 3.12 (m, 1H), 3.50 (m, 2H), 3.55 (m, 1H), 4.01 (m, 3H), 5.17 (m, 1H), 7.24 (m, 6H), 8.22 (d, 1H, J=6.9), 8.71 (d, 1H, J=3.6).

Test Example 1

(1) Measurement of Inhibitory Activity Against μ-Calpain and m-Calpain

The inhibitory activity against μ-calpain and m-calpain was assayed according to the method described in Anal. Biochem. 1993, vol. 208, p. 387-392. That is, to 2.5 μL of a DMSO solution containing a varying concentration of the test sample in a 96-well plate was added 200 μL of a reaction solution containing 0.5 mg/mL casein, 50 mM Tris-HCl buffer (pH 7.4), 20 mM dithiothreitol and 1.0 nmol μ-calpain (derived from human red blood cells; available from Cosmo Bio Co. Ltd.) or m-calpain (derived from porcine kidney; available from Cosmo Bio Co. Ltd.). After 20 mM aqueous calcium chloride (50 μL) was added thereto, the mixture was incubated at 30° C. for 60 minutes. Then, 100 μL of the reaction solution was transferred to another 96-well plate, and purified water (50 μL) and 50% aqueous solution (100 μL) of Protein Assay Dye Reagent (available from Bio-Rad Laboratories, Inc.; catalogue No. 500-600) were added thereto. The reaction mixture was allowed to stand at room temperature for 15 minutes, and its absorbance was measured at 595 nm.

The absorbance of a reaction mixture prepared in the same manner as mentioned above, except that a DMSO solution contained no sample, was used as a control value, and that of a reaction mixture prepared in the same manner as mentioned above, except that 1 mM aqueous EDTA solution (50 μL) was used in place of 20 mM aqueous calcium chloride, was used as a blank value. Inhibition rate was calculated by means of the following equation, and the concentration required for 50% inhibition ($IC_{50}$) was determined.

Inhibition rate (%)={1−(measured value minus blank value)/(control value minus blank value)}×100

The calpain inhibitory activities are shown in Table 1, which indicates that the compounds of the present invention strongly inhibited activities of μ-calpain and m-calpain.

TABLE 1

| | Enzyme inhibitory activity (μM) | |
|---|---|---|
| Compound No. | μ-calpain | m-calpain |
| Compound 1 | 0.17 | 0.11 |
| Compound 2 | 0.15 | 0.11 |
| Compound 3 | 0.25 | 0.16 |
| Compound 4 | 0.11 | 0.10 |
| Compound 5 | 0.09 | 0.05 |
| Compound 6 | 0.12 | 0.13 |
| Compound 7 | 0.10 | 0.07 |
| Compound 8 | 0.17 | 0.08 |
| Compound 9 | 0.10 | 0.14 |
| Compound 10 | 0.45 | 0.34 |
| Compound 11 | 0.17 | 0.12 |
| Compound 12 | 0.18 | 0.11 |
| Compound 13 | 0.30 | 0.20 |
| Compound 14 | 0.16 | 0.20 |
| Compound 15 | 0.18 | 0.14 |
| Compound 16 | 0.14 | 0.10 |
| Compound 17 | 0.17 | 0.10 |
| Compound 18 | 0.19 | 0.12 |
| Compound 19 | 0.22 | 0.17 |
| Compound 20 | 0.42 | 0.19 |
| Compound 21 | 0.08 | 0.11 |
| Compound 22 | 0.09 | 0.16 |

TABLE 1-continued

| Compound No. | Enzyme inhibitory activity (μM) | |
| --- | --- | --- |
| | μ-calpain | m-calpain |
| Compound 23 | 0.19 | 0.18 |
| Compound 24 | 0.029 | 0.017 |

Test Example 2

Solubility

Solubility of the compounds of the present invention in 10 mM phosphate buffer (pH 7.0) was measured. The solubility of the compounds of the present invention is shown in Table 2.

TABLE 2

| Compound No. | Solubility (mg/mL) |
| --- | --- |
| 1 | 1.2 |
| 2 | 1.0 |
| 3 | 0.84 |
| 4 | 1.3 |
| 6 | 0.76 |
| 7 | 0.33 |
| 12 | 0.74 |
| 14 | 0.33 |
| 17 | 0.65 |
| 18 | 5.4 |
| 19 | 8.3 |
| 20 | 16.3 |

Test Example 3

Permeability Test with Caco-2 Cells $1\times10^5/cm^2$ of Caco-2 cells (Catalog No. HTB-37, available from ATCC, passage number: 56) were seeded into a culture insert (polycarbonate porous filter: FALCON (trade mark) 3096, pore diameter 3 μm; area 0.31 cm²), and incubated for 22 days under the conditions of 37° C. and 5% $CO_2$ to prepare a monolayer cell. As a culture medium for the incubation, Dulbecco's modified Eagle's minimum essential medium (GIBCO BRL) supplemented with 10% fetal calf serum (GIBCO BRL), antibiotic-antimycotic mixture, liquid (GIBCO BRL), non-essential amino acid solution (GIBCO BRL) and 2 mmol/L L-glutamine (GIBCO BRL) was used. The cells were preincubated in advance in a Hanks' Balanced Salt Solution (apical membrane side: pH 6.5, basolateralt membrane side: pH 7.4) containing no sample or no control substance at 37° C. for one hour. A Hanks' Balanced Salt Solution (pH 6.5, 37° C.) containing a 10 μm sample or a control substance was run to the apical membrane side (250 μL), and the sample (950 μL) permeated through the basolateral membrane was quantified. That is, 500 μL was collected from the basolateral membrane side after one or two hours, and the permeation coefficient was measured. Propranolol was used as a positive control, and $^{14}C$-mannitol was used as a negative control. LC-MS/MS was used for quantitative analysis of samples, and a liquid scintillation counter was used for quantitative analysis of $^{14}C$-mannitol.

An amount of the sample or the control substance which had been permeated through the basolateral membrane of Caco-2 monolayer cells was determined, and apparent permeation coefficient ($P_{app}$) was calculated according to the formula:

$P_{app}=(\delta Q/\delta t)\times(1/60AC_0)$.

$P_{app}$: apparent permeation coefficient (cm/sec)
$\delta Q/\delta t$: permeation velocity (pmol/min)
A: area of monolayer cell=0.33 cm²
$C_0$: initial concentration at apical membrane side (pmol/mL)

Test Example 4

Measurement of Partition Coefficient Using IAM Column

Analysis by HPLC system was carried out under the conditions given below, and retention time of each substance was measured.

Column: IAM Fast Screening Mini-Column (Regis Technologies, Inc.)
Mobile phase: Dulbecco's phosphate buffer (pH 7.4)
Detection wavelength: 250 nm
Column temperature: room temperature
Injection amount: 5.0 to 20 μL
Flow rate: 0.5 mL/min
Sample solution: 5 mg of sample was dissolved in 100 μL of acetonitrile, and a mobile phase was added to make 1 mL of a sample solution.

The measured value was inserted into the following formula, and the partition coefficient ($K'_{IAM}$) was calculated.

$k'_{IAM}=(t_R-t_0)/t_0$ $t_0$: retention time of the peak derived from acetonitrile
$t_R$: retention time of the peak of the sample The membrane permeability of the compounds of the present invention was evaluated on the basis of the partition coefficient ($K'_{IAM}$) calculated from the permeability through Caco-2 cell membrane ($P_{app}$ (apical membrane side → basolateral membrane side)) and/or the correlated retention time in IAM column analysis.

The results of Caco-2 cell permeability assay showed that all compounds measured showed $P_{app}=10^{-6}$ or higher, a value indicating that the permeability is not a rate-limiting step in absorption. Also, an IAM column analysis revealed that the compound tested showed $k'_{IAM}=0.7$ or higher, which was considered to be equivalent to Caco-2 cell permeability of $P_{app}=10^{-6}$. According to these results, it was considered that oral administration would not cause any problem on membrane permeability in the digestive tract during absorption.

TABLE 3

| Compound | Caco-2$P_{app(a-b)}$ (cms$^{-1}$) × 10$^{-6}$ | IAM (Log k'$_{IAM}$) |
| --- | --- | --- |
| Compound 4 | 2.7 | 1.20 |
| Compound 7 | 6.3 | 1.28 |
| Compound 9 | 10.5 | 1.70 |
| Compound 15 | 4.5 | 1.36 |
| Compound 17 | — | 1.27 |
| Compound 18 | — | 1.38 |
| Compound 19 | — | 1.44 |
| Propranolol | 8.5 | 1.95 |
| $^{14}C$-Mannitol | 0.6 | — |

Test Example 5

Measurement of Transportation Rate into Blood

The compound of the present invention was administered orally to Macaca fascicularis (crab-eating monkey) at a dose of 10 mg/kg. The blood was collected with the lapse of time, and the concentration of each compound in the plasma was measured. The maximum plasma concentration ($C_{max}$) and the area under the blood concentration-time curve (AUC) were shown in Table 4.

When the compound of the present invention was administered orally, it was transported into the blood with a higher enzyme inhibitory activity ($IC_{50}$) than that shown in Test Example 1, elucidating that the compound of the present invention has excellent pharmakokinetics.

TABLE 4

| | Pharmakokinetics | |
|---|---|---|
| Compound No. | $C_{max}$ (µM) | AUC$_{0 \to 4\,hr}$ (µM · hr) |
| Compound 2 | 0.59 | 0.61 |
| Compound 4 | 1.2 | 1.9 |
| Compound 7 | 0.65 | 0.87 |
| Compound 17 | 1.1 | 2.4 |
| Compound 18 | 0.66 | 1.6 |
| Compound 19 | 0.90 | 1.6 |

Experimental Example 6

Effect on Rat Retinal Ischemia Reperfusion Injury

Male SD rats (body weight: 150-200 g, purchased from Charles River Japan, Inc.) were used. For anesthesia, a mixture of equivalent amounts of 50 mg/mL ketamine injection and 20 mg/mL xylazine injection was administered intramuscularly at 1.0 mL/Kg body weight into the femora of the rats 15 minutes before ischemia. To achieve ischemia, the optic nerve including central retinal artery was ligated using a Sugita Clip minitype (No. 98), and the blood flow was blocked for 55 minutes. Such ligation was released 55 minutes after the above ligation, and blood flow was made to run again into retina (hereinafter, referred to as ischemia reperfusion). For normal group, central retinal artery was only exposed and ischemia was not set up. After 7 days from reperfusion in ischemia, a tissue specimen was prepared. For preparation of the tissue specimen, an excess amount of pentobarbital solution was intraperitoneally administered to sacrifice the animal, and eyeball was enucleated. The enucleated eyeball was dipped and fixed for 24 hours in a fixing solution of 2% paraformaldehyde and 2.5% glutaraldehyde (0.1 M phosphate buffer, pH 7.4). After fixing, a paraffin embedded block of eyeball was prepared, and such a paraffin embedded eyeball was sliced with a microtome in a thickness of 3 µm at the section passing through the center of the optic disc. The sections were stained with hematoxylin and eosin (HE) in a conventional manner. The stained sections were observed under an optical microscope, and ganglion cells of retina per 0.25 mm width of retina section at 1-2 mm from the center of the optic disc were counted.

Compound 17 was used as a drug to be tested. A solution obtained by dissolving sodium carboxymethylcellulose in distilled water to a concentration of 0.5% (CMC solution) was orally administered to the control group, and a solution obtained by suspending Compound 17 in a CMC solution at 1.0%, such that Compound 17 was administered at 100 mg/Kg body weight, was orally administered to the drug group, both at 15 minutes before start of ischemia and immediately after release from ischemia (Compound 17 administration group). A CMC solution was administered to control group and normal group in a similar manner.

The results thereof are shown in FIG. 1. The ganglion cell count decreased to about ¼ of that of the normal group (control group) due to ischemia reperfusion. In contrast, Compound 17 administration (drug group) significantly suppressed the decrease due to ischemia reperfusion in the ganglion cell count. The above results suggest that Compound 17 of the present invention has an effect to improve retinal ischemic disorder.

Formulation Example 1

Tablet

| | |
|---|---|
| Compound 4 | 5 g |
| Starch | 12 g |
| Lactose | 27.2 g |
| Magnesium Stearate | 0.4 g |

Compound 4, starch and lactose were blended well, and formulated into granules for tableting according to the wet granule tableting method. After addition of magnesium stearate, the granules were compressed to make 400 tablets. The tablets were, if required, coated with an enteric coating agent (methacrylic acid copolymer).

Formulation Example 2

Eye Drops

| | |
|---|---|
| Compound 18 | 100 mg |
| Boric acid | 700 mg |
| Borax | q.s. |
| Sodium chloride | 500 mg |
| Sodium edetate | 0.05 mg |
| Benzalkonium chloride | 0.0005 mg |
| Sterile purified water | total volume of 100 ml |

The above components were mixed under sterile conditions according to the conventional method to prepare eye drops.

Formulation Example 3

Injection

| | |
|---|---|
| Compound 17 | 100 mg |
| Sodium chloride | 900 mg |
| 1N Sodium hydroxide | q.s. |
| Distilled water for injection | total volume 100 mL |

The above components were mixed under sterile conditions according to the conventional method to prepare an injection preparation.

INDUSTRIAL APPLICABILITY

Since the compounds of the formula (I) of the present invention have excellent calpain inhibitory activity and good oral absorbability, they are useful as a prophylactic and therapeutic agent for various diseases related to calpain such as ischemic disease, immunologic disease, multiple sclerosis Alzheimer's disease, osteoporosis, diseases caused by brain tissue damage, cataract, glaucoma, retinal disease, retinochoroiditis (diabetic retinopathy, retinal vein occulusion, macular degeneration, retinitis pigmentosa, hypertensive retinopathy, retinal detachment, etc.), posterior eyeball complications due to photocoagulation or a disease involving neovascularization.

The invention claimed is:

1. A compound represented by the formula (I)

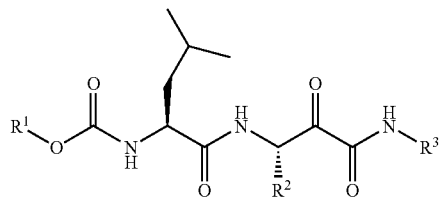

(I)

wherein $R^1$ is (1) a group represented by the formula (IIb) in which n is an integer of 2 to 5,

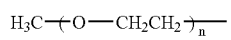

(IIb)

(2) a straight or branched $C_{1-6}$ alkyl substituted by a pyridyl group optionally having a $C_{1-3}$ alkyl substituent on the pyridine ring, or (3) a tetrahydrofuranyl group or a tetrahydropyranyl group;

$R^2$ is a straight or branched $C_{1-6}$ alkyl, optionally substituted by a phenyl; and $R^3$ is hydrogen, a straight or branched $C_{1-6}$ alkyl or is selected from the group consisting of cyclopropyl, cyclobutyl, cyclopentyl and cyclohexyl.

2. The compound as claimed in claim 1, wherein $R^1$ is a group of the formula (IIb)

(IIb)

in which n is an integer of 2 to 5.

3. The compound as claimed in claim 1, wherein $R^3$ is cyclopropyl.

4. The compound of claim 1 selected from the group consisting of ((1S)-1-((((1S)-1-benzyl-2,3-dioxo-3-(cyclopropylamino)propyl)amino)carbonyl)-3-methylbutyl)carbamic acid 5-methoxy-3-oxapentyl ester, ((1S)-1-((((1S)-1-benzyl-2,3-dioxo-3-(cyclopropylamino)propyl)amino)carbonyl)-3-methylbutyl)carbamic acid 8-methoxy-3,6-dioxaoctyl ester, ((1S)-1-((((1S)-1-benzyl-2,3-dioxo-3-(cyclopropylamino)propyl)amino)carbonyl)-3-methylbutyl)carbamic acid 11-methoxy-3,6,9-trioxaundecanyl ester, or ((1S)-1-((((1S)-1-benzyl-3-(cyclopropylamino)-2,3-dioxopropyl)amino)carbonyl)-3-methylbutyl)carbamic acid 2-(pyridin-2-yl)ethyl ester.

5. A medicament comprising the compound as claimed in claim 1.

6. The compound as claimed in claim 1, which is ((1S)-1-((((1S)-1-benzyl-2,3-dioxo-3-(cyclopropylamino)propyl)amino)carbonyl)-3-methylbutyl)carbamic acid 5-methoxy-3-oxapentyl ester.

* * * * *